US009173711B2

(12) United States Patent
Butler et al.

(10) Patent No.: US 9,173,711 B2
(45) Date of Patent: Nov. 3, 2015

(54) CARDIAC IMPLANT MIGRATION INHIBITING SYSTEMS

(71) Applicant: BIOVENTRIX, INC., San Ramon, CA (US)

(72) Inventors: William Butler, San Ramon, CA (US); Kevin Van Bladel, Livermore, CA (US); Ernie Heflin, Pleasanton, CA (US); Lon Annest, New York, NY (US); Rovil Arcia, Fremont, CA (US); John Bower, Livermore, CA (US)

(73) Assignee: BioVentrix, Inc., San Ramon, CA (US)

( * ) Notice: Subject to any disclaimer, the term of this patent is extended or adjusted under 35 U.S.C. 154(b) by 333 days.

(21) Appl. No.: 13/632,106

(22) Filed: Sep. 30, 2012

(65) Prior Publication Data
US 2013/0090672 A1 Apr. 11, 2013
Related U.S. Application Data

(60) Provisional application No. 61/541,978, filed on Sep. 30, 2011, provisional application No. 61/541,975, filed on Sep. 30, 2011, provisional application No. 61/541,980, filed on Sep. 30, 2011, provisional application No. 61/541,624, filed on Sep. 30, 2011.

(51) Int. Cl.
*A61F 2/24* (2006.01)
*A61B 19/00* (2006.01)
(Continued)

(52) U.S. Cl.
CPC .................. *A61B 19/22* (2013.01); *A61B 17/00* (2013.01); *A61B 17/0057* (2013.01);
(Continued)

(58) Field of Classification Search
CPC ... A61F 2/2478; A61F 2/2481; A61F 2/2487; A61B 2017/0401; A61B 2017/0417; A61B 2017/048; A61B 19/22; A61B 17/00; A61B 17/0057; A61B 17/3417; A61B 17/3478; A61B 17/0485; A61B 2017/00243; A61B 2017/3458; A61B 2017/0409; A61B 2017/22038; A61B 2017/22065; A61B 2017/306; A61B 2017/3488; A61B 2018/1425; A61M 28/02
USPC .............. 600/16, 37; 606/151, 213, 214, 215, 606/232
See application file for complete search history.

(56) References Cited

U.S. PATENT DOCUMENTS 4,007,743 A 2/1977 Blake
5,295,958 A 3/1994 Shturman
(Continued)

FOREIGN PATENT DOCUMENTS

EP 1 078 644 A1 2/2001
WO 00/06028 A1 2/2000
(Continued)

OTHER PUBLICATIONS

USPTO—STIC Search Results—NPL (Dec. 11, 2014).*
(Continued)

*Primary Examiner* — Ryan Severson
*Assistant Examiner* — Christian Knauss
(74) *Attorney, Agent, or Firm* — Kilpatrick Townsend & Stockton LLP

(57) ABSTRACT

Medical devices, systems, and methods reduce the distance between two locations in tissue, often for treatment of congestive heart failure. In one embodiment an anchor of an implant system may reside within the right ventricle in engagement with the ventricular septum. A tension member may extend from that anchor through the septum and an exterior wall of the left ventricle to a second anchor disposed along an epicardial surface. Deployment of the anchor within the right ventricle may be performed by inserting a guidewire through the septal wall into the right ventricle. The anchor may be inserted into the right ventricle over the guidewire and through a lumen of a catheter. An anchor force may be applied within a desired range to secure the anchors about the septum and epicardial surface. The anchor force may inhibit migration of the anchors relative to the septum and epicardial surface.

30 Claims, 40 Drawing Sheets

(51) Int. Cl.

| | |
|---|---|
| *A61B 17/00* | (2006.01) |
| *A61M 29/02* | (2006.01) |
| *A61B 17/04* | (2006.01) |
| *A61B 17/22* | (2006.01) |
| *A61B 17/30* | (2006.01) |
| *A61B 17/34* | (2006.01) |
| *A61B 18/14* | (2006.01) |

(52) U.S. Cl.
CPC .......... *A61B 17/0401* (2013.01); *A61F 2/2487* (2013.01); *A61M 29/02* (2013.01); *A61B 17/0485* (2013.01); *A61B 17/3417* (2013.01); *A61B 17/3478* (2013.01); *A61B 2017/00243* (2013.01); *A61B 2017/0409* (2013.01); *A61B 2017/0417* (2013.01); *A61B 2017/22038* (2013.01); *A61B 2017/22065* (2013.01); *A61B 2017/306* (2013.01); *A61B 2017/3458* (2013.01); *A61B 2017/3488* (2013.01); *A61B 2018/1425* (2013.01)

(56) References Cited

U.S. PATENT DOCUMENTS

| | | | |
|---|---|---|---|
| 5,830,224 | A | 11/1998 | Cohn et al. |
| 5,961,440 | A | 10/1999 | Schweich, Jr. et al. |
| 6,045,497 | A * | 4/2000 | Schweich et al. ............... 600/16 |
| 6,050,936 | A | 4/2000 | Schweich, Jr. et al. |
| 6,059,715 | A | 5/2000 | Schweich, Jr. et al. |
| 6,125,852 | A | 10/2000 | Stevens et al. |
| 6,162,168 | A | 12/2000 | Schweich, Jr. et al. |
| 6,165,119 | A | 12/2000 | Schweich, Jr. et al. |
| 6,165,120 | A | 12/2000 | Schweich, Jr. et al. |
| 6,166,684 | A | 12/2000 | Yoshikawa et al. |
| 6,258,021 | B1 | 7/2001 | Wilk |
| 6,260,552 | B1 * | 7/2001 | Mortier et al. ................. 128/898 |
| 6,406,420 | B1 | 6/2002 | McCarthy et al. |
| 6,494,825 | B1 | 12/2002 | Talpade |
| 6,511,416 | B1 | 1/2003 | Green et al. |
| 6,572,529 | B2 | 6/2003 | Wilk |
| 6,616,684 | B1 * | 9/2003 | Vidlund et al. ............... 606/213 |
| 6,705,988 | B2 | 3/2004 | Spence et al. |
| 6,709,382 | B1 * | 3/2004 | Horner ............................ 600/16 |
| 6,746,471 | B2 | 6/2004 | Mortier et al. |
| 6,776,754 | B1 * | 8/2004 | Wilk ............................... 600/16 |
| 6,808,488 | B2 | 10/2004 | Mortier |
| 6,859,662 | B2 | 2/2005 | Bombardini |
| 6,890,295 | B2 | 5/2005 | Michels et al. |
| 7,146,225 | B2 | 12/2006 | Guenst et al. |
| 7,326,177 | B2 | 2/2008 | Williamson et al. |
| 7,390,329 | B2 * | 6/2008 | Westra et al. ............... 606/151 |
| 7,722,523 | B2 | 5/2010 | Mortier et al. |
| 7,753,923 | B2 | 7/2010 | St. Goar et al. |
| 7,766,816 | B2 | 8/2010 | Chin et al. |
| 7,785,248 | B2 | 8/2010 | Annest et al. |
| 8,066,766 | B2 | 11/2011 | To et al. |
| 8,123,668 | B2 | 2/2012 | Annest et al. |
| 8,268,009 | B2 * | 9/2012 | Teitelbaum et al. ....... 623/23.64 |
| 8,394,008 | B2 | 3/2013 | Annest et al. |
| 8,425,402 | B2 | 4/2013 | Annest et al. |
| 8,449,442 | B2 | 5/2013 | Annest et al. |
| 8,491,455 | B2 | 7/2013 | Annest et al. |
| 8,506,474 | B2 | 8/2013 | Chin et al. |
| 8,636,639 | B2 | 1/2014 | Annest et al. |
| 2001/0025171 | A1 * | 9/2001 | Mortier et al. ..................... 606/1 |
| 2001/0041821 | A1 | 11/2001 | Wilk |
| 2002/0058855 | A1 | 5/2002 | Schweich, Jr. et al. |
| 2002/0077524 | A1 | 6/2002 | Schweich, Jr. et al. |
| 2002/0120298 | A1 | 8/2002 | Kramer et al. |
| 2002/0123768 | A1 | 9/2002 | Gilkerson et al. |
| 2002/0169359 | A1 * | 11/2002 | McCarthy et al. ............... 600/16 |
| 2002/0169360 | A1 | 11/2002 | Taylor et al. |
| 2002/0188170 | A1 | 12/2002 | Santamore et al. |
| 2003/0032979 | A1 * | 2/2003 | Mortier et al. ................. 606/213 |
| 2003/0163165 | A1 | 8/2003 | Bornzin et al. |
| 2003/0166992 | A1 | 9/2003 | Schweich, Jr. et al. |
| 2003/0181928 | A1 * | 9/2003 | Vidlund et al. ............... 606/151 |
| 2003/0181951 | A1 | 9/2003 | Cates |
| 2003/0233022 | A1 * | 12/2003 | Vidlund et al. ................. 600/16 |
| 2004/0167580 | A1 | 8/2004 | Mann et al. |
| 2004/0225304 | A1 * | 11/2004 | Vidlund et al. ............... 606/151 |
| 2005/0065506 | A1 | 3/2005 | Phan |
| 2005/0096498 | A1 | 5/2005 | Houser et al. |
| 2005/0137688 | A1 | 6/2005 | Salahieh et al. |
| 2005/0143620 | A1 | 6/2005 | Mortier et al. |
| 2005/0192599 | A1 | 9/2005 | Demarais |
| 2005/0288613 | A1 | 12/2005 | Heil, Jr. |
| 2006/0135962 | A1 | 6/2006 | Kick et al. |
| 2006/0161040 | A1 | 7/2006 | McCarthy et al. |
| 2006/0161238 | A1 | 7/2006 | Hall |
| 2006/0178550 | A1 * | 8/2006 | Jenson ........................... 600/16 |
| 2006/0200002 | A1 | 9/2006 | Guenst |
| 2006/0241340 | A1 | 10/2006 | Schroeder et al. |
| 2006/0247672 | A1 | 11/2006 | Vidlund et al. |
| 2006/0276684 | A1 | 12/2006 | Speziali |
| 2007/0010876 | A1 | 1/2007 | Salahieh et al. |
| 2007/0049971 | A1 | 3/2007 | Chin et al. |
| 2007/0055303 | A1 | 3/2007 | Vidlund et al. |
| 2007/0073274 | A1 | 3/2007 | Chin et al. |
| 2007/0112244 | A1 | 5/2007 | McCarthy et al. |
| 2007/0161846 | A1 | 7/2007 | Nikolic et al. |
| 2007/0203503 | A1 | 8/2007 | Salahieh et al. |
| 2007/0265658 | A1 * | 11/2007 | Nelson et al. .................. 606/213 |
| 2008/0082132 | A1 * | 4/2008 | Annest et al. ..................... 607/4 |
| 2008/0097148 | A1 | 4/2008 | Chin et al. |
| 2008/0269551 | A1 | 10/2008 | Annest et al. |
| 2008/0294251 | A1 | 11/2008 | Annest et al. |
| 2009/0093670 | A1 * | 4/2009 | Annest et al. ................... 600/16 |
| 2009/0270980 | A1 | 10/2009 | Schroeder et al. |
| 2010/0010538 | A1 | 1/2010 | Juravic et al. |
| 2010/0016655 | A1 * | 1/2010 | Annest et al. ................... 600/37 |
| 2010/0057000 | A1 | 3/2010 | Melsheimer et al. |
| 2010/0268020 | A1 | 10/2010 | Chin et al. |
| 2011/0160750 | A1 | 6/2011 | Annest et al. |
| 2012/0190958 | A1 | 7/2012 | Annest et al. |
| 2013/0090523 | A1 | 4/2013 | Van Bladel et al. |
| 2013/0090684 | A1 | 4/2013 | Van Bladel et al. |
| 2013/0096579 | A1 | 4/2013 | Annest et al. |
| 2013/0324787 | A1 | 12/2013 | Chin et al. |
| 2013/0325041 | A1 | 12/2013 | Annest et al. |
| 2014/0031613 | A1 | 1/2014 | Annest et al. |
| 2014/0051916 | A1 | 2/2014 | Chin et al. |

FOREIGN PATENT DOCUMENTS

| | | |
|---|---|---|
| WO | 02/30335 A2 | 4/2002 |
| WO | 03032818 A3 | 4/2003 |
| WO | 2005092203 A1 | 10/2005 |
| WO | 2006044467 A2 | 4/2006 |
| WO | 2007/022519 A2 | 2/2007 |

OTHER PUBLICATIONS

USPTO—STIC Search Results—Patents (Dec. 11, 2014).*
International Search Report and Written Opinion of PCT/US2012/058182, mailed Mar. 1, 2013, 19 pages.
International Search Report and Written Opinion of PCT/US2012/058074 mailed on Mar. 13, 2013, 18 pages.
International Report on Patentability of PCT/US2012/058074 dated Apr. 10, 2014, 8 pages.
International Report on Patentability of PCT/US2012/058176 dated Apr. 10, 2014, 11 pages.
International Search Report and Written Opinion of PCT/US2012/58176, mailed Jan. 8, 2013, 19 pages.
International Search Report and Written Opinion of PCT Application No. PCT/US12/58074, mailed Mar. 13, 2013, 18 pages.
European Examination Report of EP Patent Application 05810316.9 dated Mar. 10, 2009, 6 pages.
International Search Report and Written Opinion of PCT Application No. PCT/US06/32663, Jul. 31, 2007, 5 pages.
International Search Report and Written Opinion of PCT Application No. PCT/US2005/036690, mailed Jul. 9, 2007, 6 pages.

(56) References Cited

OTHER PUBLICATIONS

International Search Report and Written Opinion of PCT Application No. PCT/US09/51288, mailed Sep. 15, 2009, 9 pages.
International Search Report and Written Opinion of PCT Application No. PCT/US08/64255, mailed Sep. 29, 2008, 17 pages.
International Search Report and Written Opinion of PCT Application No. PCT/US06/22594, mailed Oct. 1, 2008, 9 pages.
International Search Report and Written Opinion of PCT/US2012/058106, mailed Nov. 26, 2012, 14 pages.
International Search Report and Written Opinion of PCT Application No. PCT/US08/78810, mailed Feb. 12, 2009, 11 pages.
Extended European Examination Report of EP Patent Application 06802038.7 dated Nov. 12, 2013, 13 pages.

* cited by examiner

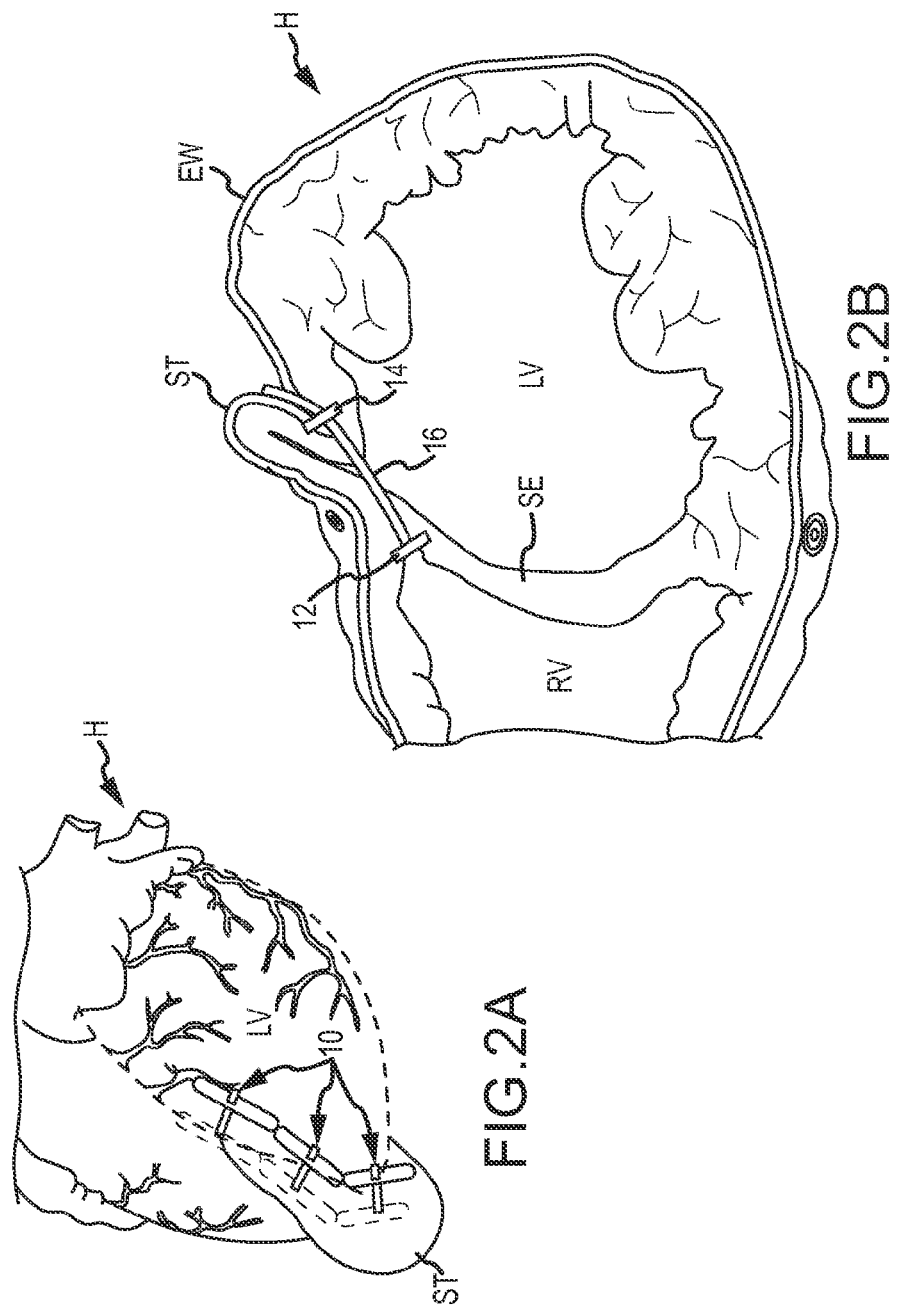

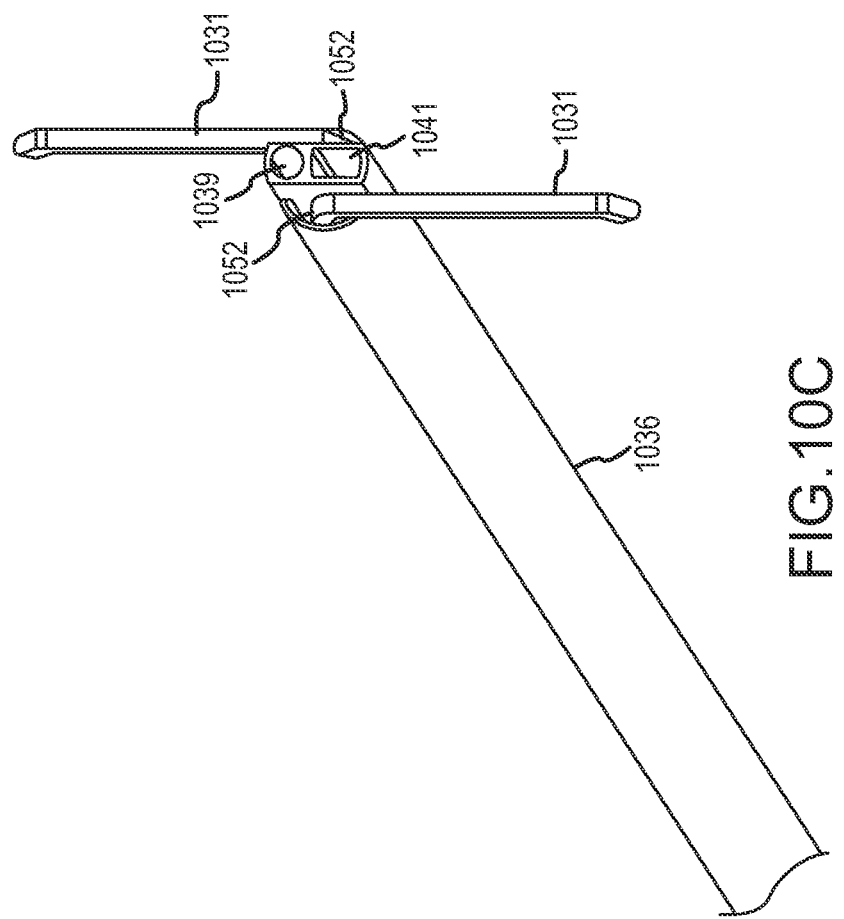

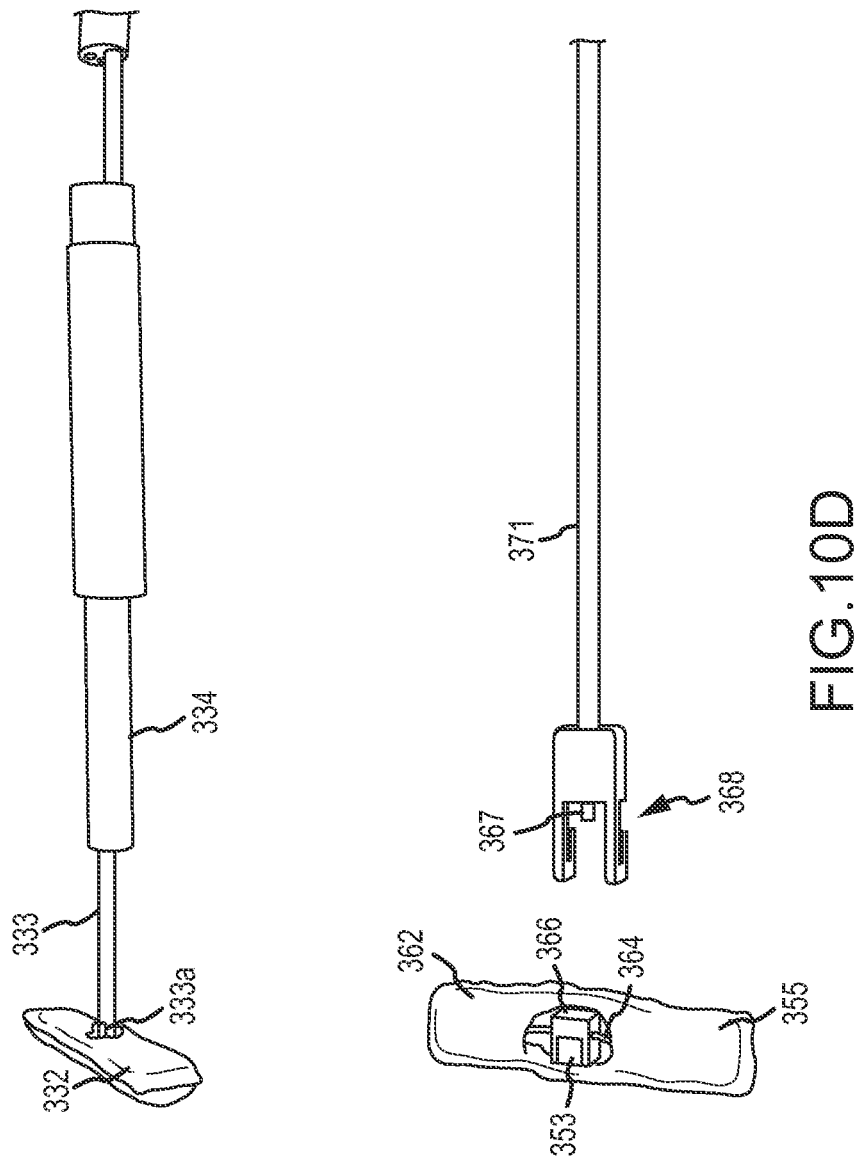

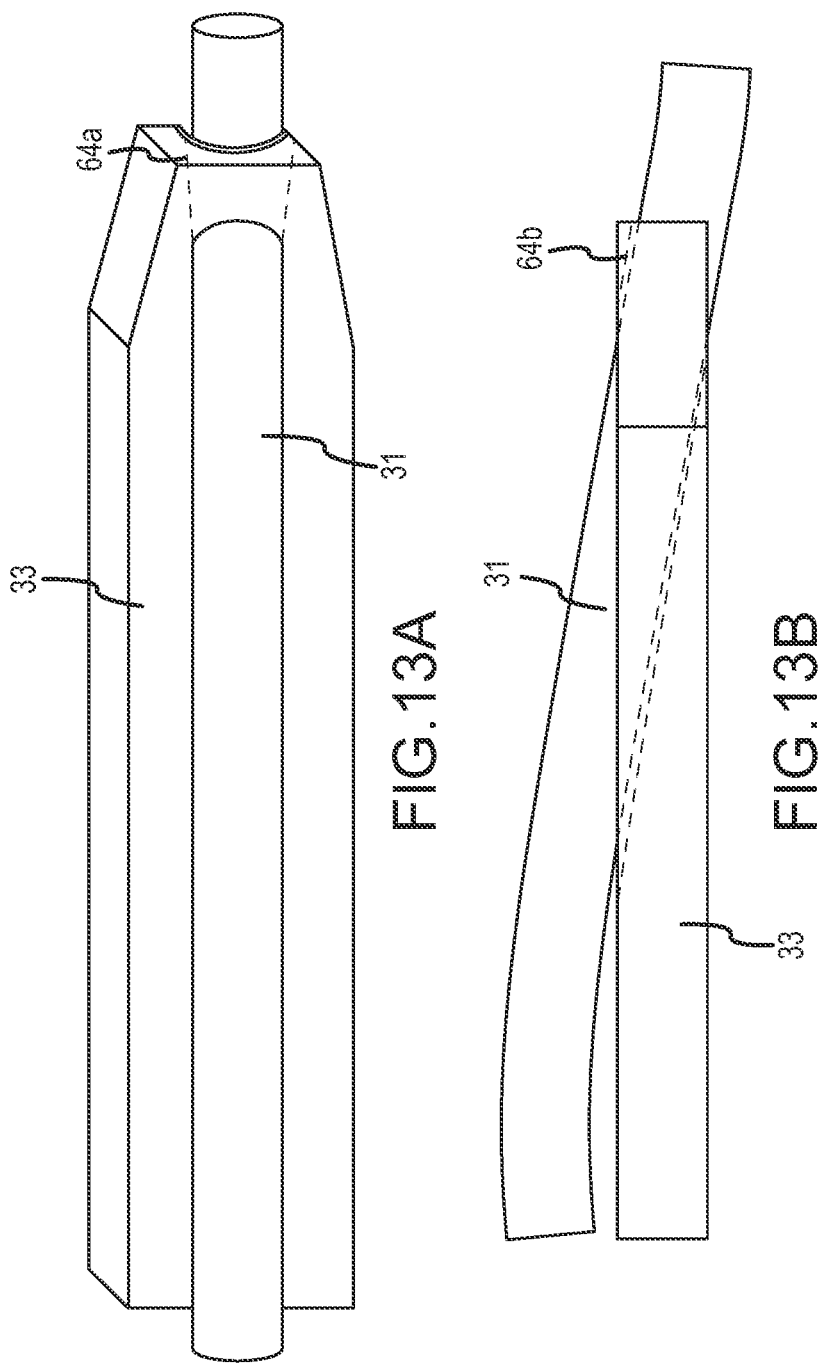

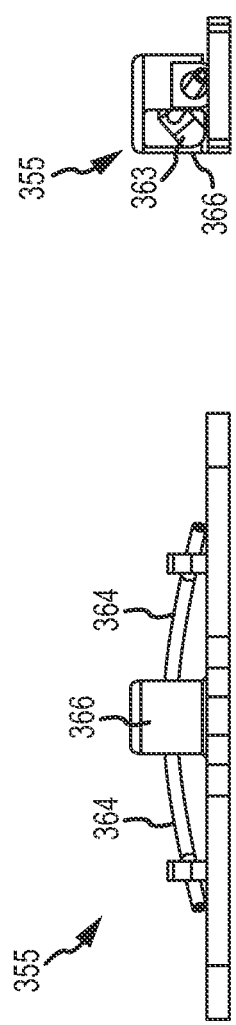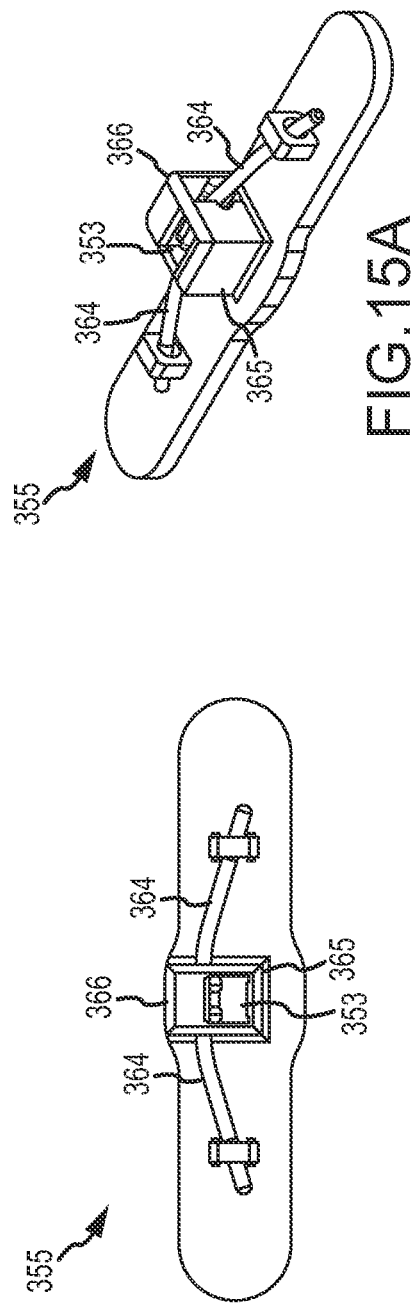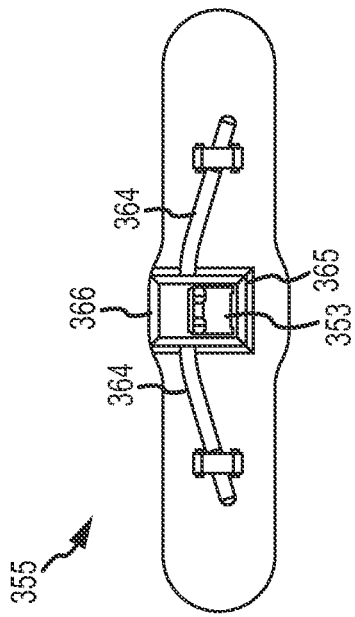

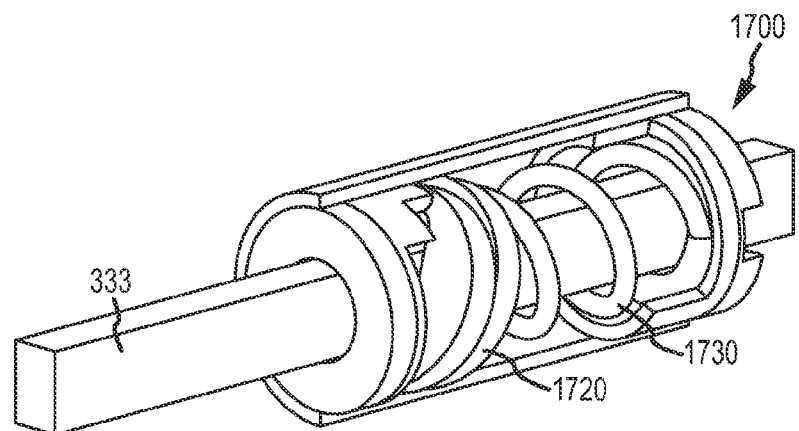
FIG. 17
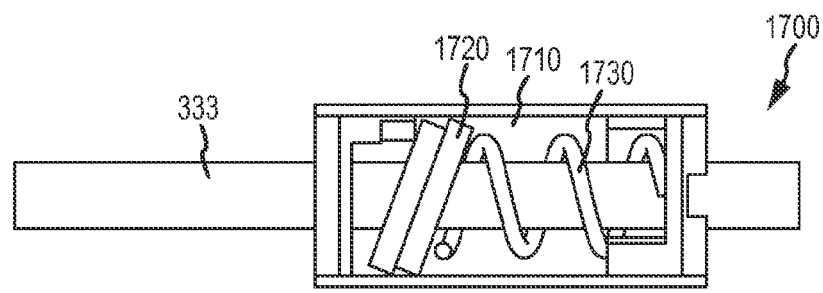
FIG. 17A
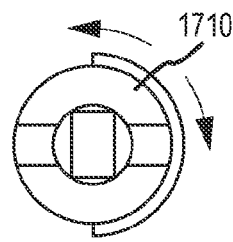 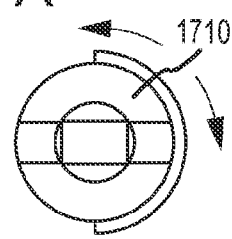
FIG. 17B  FIG. 17C

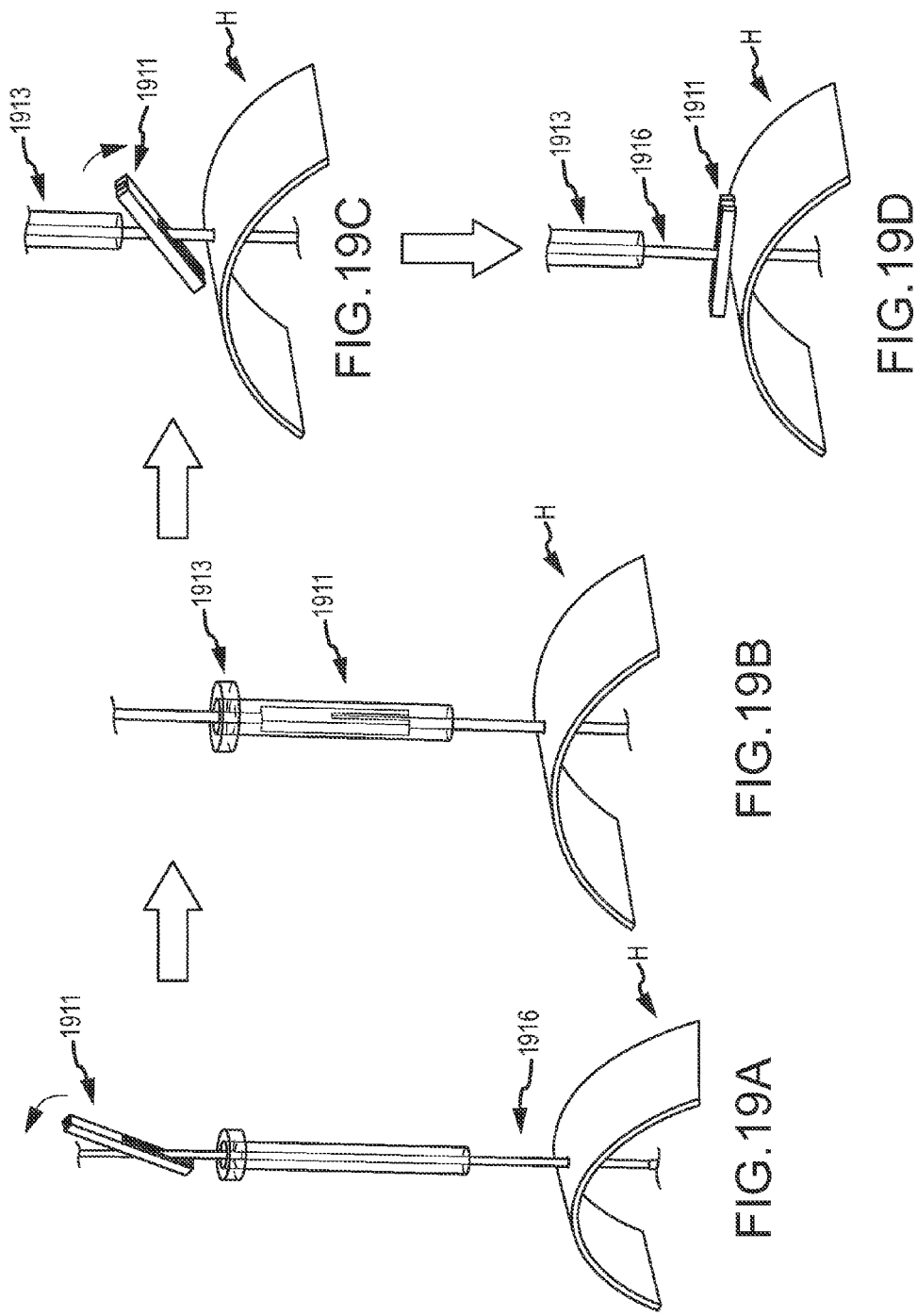

CARDIAC IMPLANT MIGRATION INHIBITING SYSTEMS

CROSS-REFERENCES TO RELATED APPLICATIONS

This application is related to and claims the benefit of U.S. Provisional Patent Application No. 61/541,978 entitled "Cardiac Implant Migration Inhibiting Systems," filed Sep. 30, 2011. This application is also related to and claims the benefit of U.S. Provisional Patent Application No. 61/541,975 entitled "Remote Pericardial Hemostasis for Ventricular Access and Reconstruction or Other Organ Therapies," filed Sep. 30, 2011; U.S. Provisional Patent Application No. 61/541,980 entitled "Over-The-Wire Cardiac Implant Delivery System for Treatment of CHF and Other Conditions," filed Sep. 30, 2011; and U.S. Provisional Patent Application No. 61/541,624 entitled "Trans-Catheter Ventricular Reconstruction Structures, Methods, and Systems for Treatment of Congestive Heart Failure and Other Conditions," filed Sep. 30, 2011; the full disclosures of which are incorporated herein by reference in their entirety.

The subject matter of this application is also related to that of US Patent Publication No. US2009/0093670, as published on Apr. 9, 2009 and entitled "Treating Dysfunctional Cardiac Tissue;" and to that of US Patent Publication No. US2010/0016655, as published on Jan. 21, 2010 and entitled "Cardiac Anchor Structures, Methods, and Systems for treatment of Congestive Heart Failure and Other Conditions;" the full disclosures of which are incorporated herein by reference in their entirety.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

An exemplary method and implant for closing off a lower portion of a heart ventricle is described in U.S. Pat. No. 6,776,754, the full disclosure of which is incorporated herein by reference. A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. US Patent Publication No. US2009/0093670 describes structures and methods for treating dysfunctional cardiac tissue, while US Patent Publication No. US2010/0016655 describes cardiac anchor structures, methods, and systems for treatment of congestive heart failure and Other Conditions. The full disclosures of all of these references are incorporated herein by reference in their entirety.

While the proposed implants, systems, and methods may help surgically remedy the size of the ventricle as a treatment of congestive heart failure and appear to offer benefits for many patients, still further advances would be desirable. In general, it would be desirable to provide improved devices, systems, and methods for treatment of congestive heart failure. It would be particularly desirable if such devices and techniques could significantly and reliably alter the shape and function of the heart using implants that do not unnecessarily damage or weaken the tissue structures. It would be also be beneficial to enhance the accuracy of ventricular reconstruction while simplifying the overall procedure, ideally while decreasing the sensitivity of the therapy on unusual surgical skills. It would be advantageous if these improvements could be provided without overly complicating the structures of implants or implant deployment systems, and while significantly enhancing the benefits provided by the implanted devices.

BRIEF SUMMARY OF THE INVENTION

Embodiments of the present invention provide improved medical devices, systems, and methods, in many cases for reducing the distance between two locations in tissue, optionally in a less or minimally invasive manner. The present invention may find specific use in the treatment of a failing heart, particularly for the alleviation of congestive heart failure and other progressive heart diseases by reconfiguring abnormal heart geometry that may be contributing to heart dysfunction. In many embodiments, implant components will be positioned at least partially within a chamber of the heart. For example, an anchor of an implant system may, when the system is fully deployed, reside within the right ventricle in engagement with the ventricular septum. A tension member may extend from that anchor through the septum and an exterior wall of the left ventricle to a second anchor along an epicardial surface of the heart. Despite deployment of the implants while the heart is beating, the implants can be deployed so as to close off a portion of the ventricle without applying so much force as to eventually pull through the tissue of the diseased heart by allowing at least one of the anchors to slide freely along the tension member while a force within a desired range is applied, and then locking the sliding anchor so as to inhibit movement of the anchors away from each other. Perforating both the exterior wall and the septum from an epicardial approach can provide beneficial control over the effective reshaping of the ventricular chamber.

In a first aspect, the invention provides a method for inhibiting migration of anchors of a heart implant device. The method may include positioning a first anchor in engagement with a first wall of the heart, the first anchor being coupled with a tension member. The method may also include positioning a second anchor in engagement with a second wall of the heart, the second anchor being slidably coupled with the tension member so that the second anchor may slide proximally and distally along a length of the tension member. The method may further include applying an anchor force within a desired range between the tension member and the second anchor so that the first anchor provides a force urging the first wall toward the second wall and the second anchor provides a force urging the second wall toward the first wall. The method may additionally include securing the second anchor relative to the tension member while the anchor force is applied so as to restrict proximal movement of the second anchor along the tension member and maintain the anchor force within the desired range.

The anchor force may be applied via a tension device located partially or fully outside the heart. The anchor force applied may be measured via a force indicator of the tension device, such as indicia of the tension member. In some embodiments, the first anchor is inserted distally of the first wall over a guidewire that is inserted into the heart distally of the first wall. The first anchor may be inserted distally of the first wall in a low profile configuration and may be deployable laterally relative to the tension member to a deployed configuration where the first anchor is able to rotate relative to the tension member. The second anchor may have a variable force mode that allows the second anchor to slide axially both proximally and distally along the tension member and may also have a set force mode that inhibits movement of the second anchor proximally along the tension member.

The second anchor may include a lumen through which the tension member is inserted and a lock. The method may additionally include operating the lock to reconfigure the second anchor from the variable force mode to the set force mode, or vice versa. The lock of the second anchor may include a spring and cam disposed adjacent the lumen or a spring and lock plate disposed adjacent the lumen of an anchoring structure. The lock may be operated from outside the patent body and operating the lock may include biasing the lock plate or the cam against the tension member in the lumen.

The anchor force may be applied to the second anchor by engaging the second anchor through a lumen of the tension device. The tension device may include a compression shaft and the second anchor may be reconfigured from outside the patient body through the lumen. The tension device may include a shaft extending from a proximal end to a distal end and a lumen through which the tension member is inserted and the anchor force may be applied within the desired range by tensioning a portion of the tension member that extends proximally of the tension device. The tension device may further include a tube slidably disposed over the shaft. The tube may include a compression spring and indicia that provide an indication of the anchor force applied as the shaft is advanced distally through the tube. The indicia may indicate that anchor force is within the desired range.

The applied anchor force may be sufficient to bring the first wall into engagement with the second wall and may further be sufficient to inhibit migration of the first and/or second anchor with respect to the first and/or second wall. The anchor force may be insufficient to induce passage of the first anchor through the first wall. The method may additionally include advancing an intermediate body of an ingrowth material along the tension member so that the elongate body is disposed between the first wall and the second wall before the walls are brought into engagement, extending the body laterally from the tension member, and rotationally orienting the body by rotating the tension member, the material promoting tissue growth between the first and second wall.

In another aspect, the invention provides a method for inhibiting migration of anchors positioned adjacent walls of a chamber of a heart. The method may include inserting a first anchor distally of a first wall of the heart, which may be a wall of the septum. The first anchor may be pivotally coupled with a tension member that extends from the first anchor, across the chamber of the heart, to proximally of a second wall of the heart. The method may also include positioning a second anchor proximally of the second wall, which may be a wall of a chamber of the heart (e.g., an external wall of the left ventricle). The second anchor may be slidably coupled with the tension member in a variable force mode so that the second anchor axially slides proximally and distally along the tension member.

The method may further include advancing the second anchor distally along the tension member to urge the first wall (e.g., septum wall) toward the second wall (e.g., chamber wall) via a force applied on the first wall by the first anchor and a force applied on the second wall by the second anchor. The method may additionally include applying a desired anchor force between the first anchor and second anchor via a tension device disposed outside the heart. The desired anchor force may inhibit migration of the anchors relative to the first wall and the second wall. The method may additionally include reconfiguring the second anchor from the variable force mode to a set force mode, where the set force mode secures the second anchor relative to the tension member by inhibiting proximal movement of the second anchor along the tension member. The method may additionally include inserting the tension member through a lumen of the tension device and applying a tension force to a portion of the tension member extending proximally of the tension device.

The tension device may be configured to be disposed outside the heart while applying the force so that the first anchor provides a force to the first wall and the second anchor provides a force to the second wall, and so that the forces applied to the first and second wall are equal to the force and the force is within a predetermined range.

In another aspect, the invention provides a system for inhibiting migration of anchors of a heart implant device. The system may include a tension member having a first end and a second end. The system may also include a first anchor coupled with the tension member at the first end and the first anchor may be configured for anchoring engagement with a first wall of the heart. The system may further include a second anchor slidably couplable with the tension member. The second anchor may have a variable force mode that allows the second anchor to axially slide proximally and distally along the tension member and may have a set force mode that inhibits proximal movement of the second anchor along the tension member. The second anchor may be configured for anchoring engagement with a second wall of the heart. The system may additionally include a tension device configured to engage the second anchor so as to apply an anchor force within a desired range between the tension member and the second anchor.

The tension device may be configured to be disposed outside the heart while applying the force so that the first anchor provides a force to the first wall and the second anchor provides a force to the second wall. The tension member may include indicia of the anchor force applied between the tension member and the second anchor. The first anchor may include a proximal end, a distal end, and a lumen extending from the proximal end to the distal end through which a guidewire is inserted so that the first anchor may be inserted distally of the first wall over the guidewire. The first anchor may be pivotally coupled with the tension member so that the first anchor comprises a fixed configuration when the guidewire is inserted through the lumen and a deployed configuration when the guidewire is removed from the lumen. The fixed configuration may inhibit rotation of the first anchor relative to the tension member and the deployed configuration may allow rotation of the first anchor relative to the tension member.

The second anchor may include a lumen through which the tension member is inserted and a lock configured to change the second anchor from the variable force mode to the set force mode, or vice versa. The lock may include a spring configured to urge a cam against the tension member disposed within the lumen or a spring configured to urge a lock plate against the tension member disposed within the lumen. The anchor force may be applied to the second anchor within the desired range by engaging the second anchor through a lumen of the tension device. The tension device may include a compression shaft configured to engage the second anchor to apply the anchor force and the second anchor may be reconfigured between the variable force mode and the set force mode from outside the patient body from along or within the compressive shaft. The tension device may include a shaft comprising a proximal end, a distal end, and a lumen through which the tension member is inserted and the desired anchor force may be applied by tensioning a portion of the tension member that extends proximally from the shaft of the tension device. The tension device may further include a tube slidably disposed over the shaft. The tube may include a compression spring and indicia that provide an indication of the amount of anchor force applied as the shaft is advanced distally through the tube.

The system may additionally include an elongate flexible body of ingrowth material. The flexible body may have an aperture that slidably receives the tension member therethrough so that the body extends laterally from the tension member. The aperture may rotationally couple the elongate body to the tension member so as to facilitate orienting the elongate body by rotation of the tension member. The elongate body may be positionable between the first wall and the second wall by advancement of the body over the tension member so that the material promotes tissue growth between the first and second wall after the first and second wall are brought into engagement.

BRIEF DESCRIPTION OF THE DRAWINGS

FIG. 2A shows a reconstructed left ventricle using a series of implanted anchors so as to mitigate the deleterious effects of congestive heart failure, according to an embodiment of the invention.

FIG. 2B is a cross-sectional view of the heart of FIG. 2A, showing a reduction in the size of the left ventricle effected by one of the implants.

FIGS. 13A-13C schematically illustrate coupling of a tension member to a guidewire so as to facilitate guiding the tension member into and through the heart, according to an embodiment of the invention.

FIGS. 15A-15D illustrate various aspects of an epicardial anchor having a variable-force mode and a set force mode, according to an embodiment of the invention.

FIGS. 17-18B illustrate alternative epicardial anchors which are adapted to be advanced along and reconfigured between a variable-force mode and a set force mode via a working lumen of a minimally invasive epicardial access device, according to an embodiment of the invention.

FIGS. 19A-D illustrate insertion of an epicardial-engagement portion of an anchor over a tension member and through a working lumen of a minimally-invasive access device so as to distribute an anchoring load of an anchor lock along a desired contour, according to an embodiment of the invention.

DETAILED DESCRIPTION OF THE INVENTION

Figure 1A:
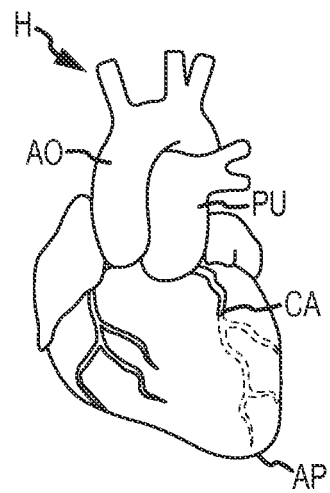
FIGS. 1A-D illustrate various views of a healthy heart and a heart having infracted tissue.

The present invention generally provides improved medical devices, systems, and methods. Exemplary embodiments of the devices are described for use in reducing the distance between a region along the septum and a region of an external wall of the left ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. For congestive heart failure therapies, perforating both the exterior wall and the septum from an epicardial approach can provide significant benefits in control over the locations of implant deployments, thereby effectively enhancing the resulting reshaping of the ventricular chamber. In some embodiments of the invention, the exterior wall and the septum may be perforated using a curved needle. The perforated septum and/or exterior wall may then be dilated to expand or enlarge the aperture through the septum or exterior wall using a dilating catheter, which may include a dilating feature such as a tapering threaded tip, cutting element (RF cutting element), and the like. The dilating catheter may dilate the aperture, such as by cutting tissue, as the dilating catheter is inserted through the exterior wall and/or septum without requiring an excessive axial force to be placed on the exterior wall and/or septum. This may reduce or eliminate arrhythmia or other negative conditions caused by excessive axial pressure exerted on the exterior wall and/or septum. In addition, this wall and/or septum perforation process can be performed while the heart is beating.

In another embodiment, guiding or deploying an implant may involve both the epicardial access path and another access path into and via an access path through the right ventricle. This additional right atrial access path into the heart may be via the superior vena cava, the inferior vena cava, the right atrial appendage, or the like, and the pathways may be joined together by coupling of a snare to a guidewire or the like within the right ventricle, the right atrium, the right pulmonary artery, or the like. While a variety of tools will be described herein for providing access pathways, for joining pathways together within the heart, for deploying implants, for maintaining hemostasis, and the like, it should be recognized that alternative embodiments may employ additional or alternative structures, some of which may be off-the-shelf, and some of which may be new structures configured particularly for use in the advantageous therapies described herein. For example, embodiments of the systems, implants, and techniques described herein may employ components described in US2009/0093670, as published on Apr. 9, 2009 and entitled "Treating Dysfunctional Cardiac Tissue;" and/or in US Patent Publication No. US2010/0016655, as published on Jan. 21, 2010 and entitled "Cardiac Anchor Structures, Methods, and Systems for treatment of Congestive Heart Failure and Other Conditions;' the full disclosures of which are incorporated herein by reference in their entirety.

Deployment of an anchor within the heart (e.g., the right ventricle) both along a single pathway or joined pathways described above may be improved by guiding the anchor into the heart over a guidewire. The anchor and/or a tether coupled to the anchor may include a lumen through which the guidewire is inserted that aligns and controls the placement of the anchor within the heart and/or controls deployment of the anchor within the heart. Such placement of the anchor and/or control of the anchor may prevent or reduce the anchor from entangling or interfering with sensitive heart tissues, such as valve leaflets, chordae, and the like. The guidewire may be positioned within a chamber of the heart (ventricle or atrium), within an artery (e.g., the pulmonary artery), and the like, and the anchor can be advanced to that position over the guidewire so as to avoid sensitive heart tissues. In embodiments where separate pathways are joined, the anchor may be inserted along one pathway, advanced over the guidewire to within a chamber of the heart, and a tether coupled with the anchor may be advanced to a position exterior to the heart along the other pathway. The tether may then be tensioned to urge a wall of the heart toward a second wall (e.g., urge the septum toward an exterior wall of the left ventricle).

Tensioning of the tether and/or anchor and the resulting reshaping of the heart may be improved using a tensioning device and/or second anchor as described herein. The second anchor may be coupled with the tension member and may include a variable-force mode that allows the second anchor to be advanced distally and proximally along the tension member; similarly, the second anchor may also include a set force mode that allows the anchor to only be advanced proximally or distally along the tension member (i.e., that inhibits proximal or distal movement of the anchor along the tension member). The second anchor may be reconfigured between the variable-force and set force mode. The tension member, second anchor, and/or first anchor may be tensioned via a minimally invasive tension device or force-application tool. The tension device/force-application tool may be designed to tension the tension member, second anchor, and/or first anchor while the heart is beating and may be designed to reconfigure the second anchor between the variable-force and set force mode from outside the patient body. The tension device may provide an indication of the tension force applied, which provides controls over the tension applied so as to inhibit migration of the first and/or second anchors with respect to the septum and/or exterior wall of the heart.

The implants can be deployed while the heart is beating. Despite deployment of the implants while the heart is beating, the implants can be deployed so as to close off a portion of the ventricle without applying so much force as to eventually pull through the tissue of the diseased heart by allowing at least one of the anchors to slide freely along the tension member while a force within a desired range is applied, and then locking the sliding anchor so as to inhibit movement of the anchors away from each other. Perforating both the exterior wall and the septum from an epicardial approach can provide beneficial control over the effective reshaping of the ventricular chamber.

Figure 1B:
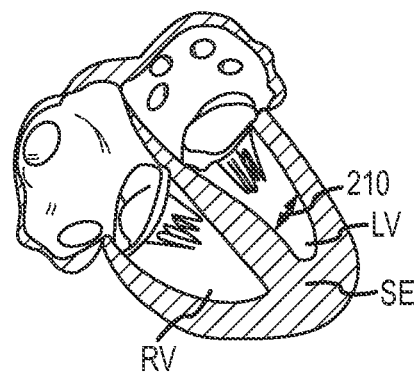

Referring now to the figures, FIG. 1A shows a normal heart H and FIG. 1B shows the cross-section of normal heart H. Normal heart H includes structures such as the aorta AO, pulmonary artery PU, coronary artery CA, apex AP, right ventricle RV, left ventricle LV with a radius 210, and septum SE.

Figure 1C:
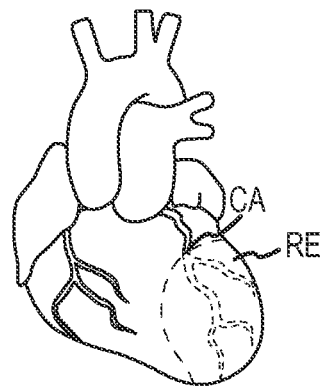
Figure 1D:
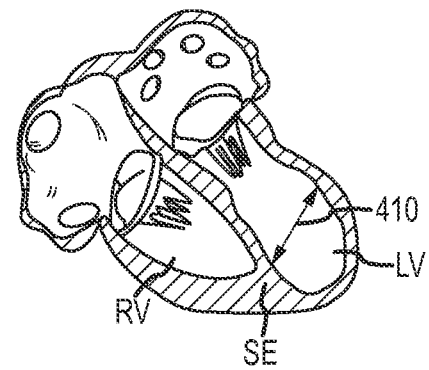

Myocardial infarction and the resultant scar formation is often the index event in the genesis of congestive heart failure ("CHF"). The presence of the scar, if left untreated, may lead to a compensatory neuro-hormonal response by the remaining, non-infarcted myocardium. FIG. 1C shows a region RE (bordered by a dotted line) of left ventricle LV which includes scar tissue. With congestive heart failure, the left ventricle often dilates or increases in size as shown in FIG. 1D, in which radius 210 has increased to a radius 410. This increase in size can result in a significant increase in wall tension and stress. With disease progression, the volume of the left ventricle LV gradually increases while forward blood flow gradually decreases, with scar tissue expanding while unscarred muscle dilates and becomes thin, losing contractility. The systems, methods, and devices described herein may be applied to inhibit, reverse, or avoid this response altogether, often halting the destructive sequence of events which could otherwise cause the eventual failure of the remaining functional heart muscle.

CHF is a condition in which the heart does not pump enough blood to the body's other organs. CHF may result from narrowing of the arteries that supply blood to the heart muscle, for instance, the coronary artery CA as shown in FIGS. 1 and 1C. Other causes of CHF include high blood pressure, heart valve dysfunctions due to degenerative processes or other causes, cardiomyopathy (a disease of the heart muscle itself), congenital heart defects, infections of the heart tissues, and the like. In certain pathological conditions, the ventricles of the heart can become ineffective in pumping the blood, causing a back-up of pressure in the vascular system behind the ventricle. The reduced effectiveness of the heart may be due to an enlargement of the heart. For example, the left ventricular radius 210 of a heart H, as shown in FIGS. 1 and 1B, may eventually increase to a larger left ventricular radius 410 of a failing heart H, as shown in FIGS. 1C and 1D.

Acute myocardial infarction (AMI) due to obstruction of a coronary artery CA is a common initiating event that can lead ultimately to heart failure. A myocardial ischemia may cause a portion of a myocardium of the heart to lose its ability to contract. Prolonged ischemia can lead to infarction of a portion of the myocardium (heart muscle). Once this tissue dies, it no longer acts as a muscle and cannot contribute to the pumping action of the heart. When the heart tissue is no longer pumping effectively, that portion of the myocardium is said to be hypokinetic or akinetic, meaning that it is less contractile or acontractile relative to the uncompromised myocardial tissue. As this situation worsens, the local area of compromised myocardium may bulge out as the heart contracts, further decreasing the hearts ability to move blood forward and dilating a ventricle. This bulged out myocardium can be seen in region RE as shown bordered by a dotted line in FIG. 1C.

As shown in FIGS. 1C and 1D, one problem with a large dilated left ventricle is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilation is greater than the hypertrophy and the result is a rising wall tension requirement for systolic contraction. This rising wall tension requirement may be an ongoing insult to the muscle myocytes (heart muscle cells), resulting in further muscle damage. In response, the heart tissue often remodels to accommodate the chronically increased filling pressures, further increasing the work that the now-compromised myocardium must perform. This vicious cycle of cardiac failure may result in the symptoms of CHF such as shortness of breath on exertion, edema in the periphery, nocturnal dyspnea (a characteristic shortness of breath that occurs at night after going to bed), weight gain, and fatigue, to name a few. The increase in wall stress also occurs during throughout the cardiac cycle and inhibits diastolic filling. The stress increase requires a larger amount of oxygen supply, which can result in exhaustion of the myocardium leading to a reduced cardiac output of the heart.

Embodiments of the invention may build on known techniques for exclusion of the scar and volume reduction of the ventricle. Unlike known techniques that are often accomplished through open surgery, including left ventricular reconstruction, ventricular restoration, the Dor procedure, and the like, the treatments described herein will often (though not necessarily always) be implemented in a minimally invasive or less invasive manner. Embodiments of the invention can provide advantages similar to those (for example) of surgical reconstruction of the ventricle, resulting in improved function due to improved dynamics, and by normalizing the downward cycle initiated by the original injury and mediated by the neuro-hormonal disease progression response.

Advantageously, the methods, devices, and systems described herein may allow percutaneous left ventricular scar exclusion and ventricle volume reduction to be applied at any appropriate time during the course of the disease. Rather than merely awaiting foreseeable disease progression and attempting to alleviate existing cardiac dysfunction, the techniques described herein may be applied proactively to prevent some or all of the heart failure symptoms, as well as to reverse at least a portion of any existing congestive heart failure effects, to limit or halt the progression of congestive heart failure, and/or to retard or prevent congestive heart failure disease progression in the future. Some embodiments may, for appropriate patients, limit the impact of myocardial infarction scar formation before heart failure even develops.

Referring now to FIGS. 2A and 2B, a series of implants 10 are shown implanted in a heart H so as to decrease a cross-section of a left ventricle LV. Each implant 10 generally includes a first anchor 12, a second anchor 14, and a tension member 16 coupling the anchors together. Tension in the tension member 16 is transferred from the anchors 12, 14 to the septum S and the external wall EW bordering the left ventricle LV so as to bring these structures into engagement, thereby effectively excluding a region of scar tissue ST from the left ventricle. In many embodiments described herein, implant 10 will be deployed by penetrating the external wall EW and septum SE via a pericardium P of the heart H, and also by accessing a right ventricle RV via a right atrium. Anchors deployed within a right ventricle and/or in engagement with the septum SE may sometimes be referred to herein as septal anchors, while anchors deployed along the external wall EW of the left ventricle LV may be referred to as epicardial anchors.

Figure 2C:
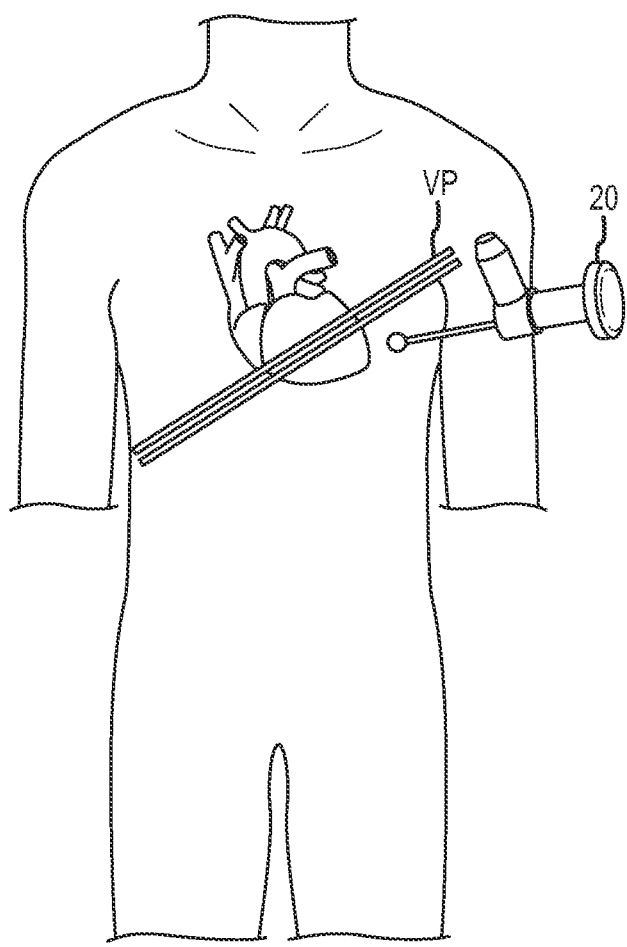
FIGS. 2C-2D schematically illustrate minimally invasive access to and endoscopic imaging of a pericardium of the heart.
Figure 2D:
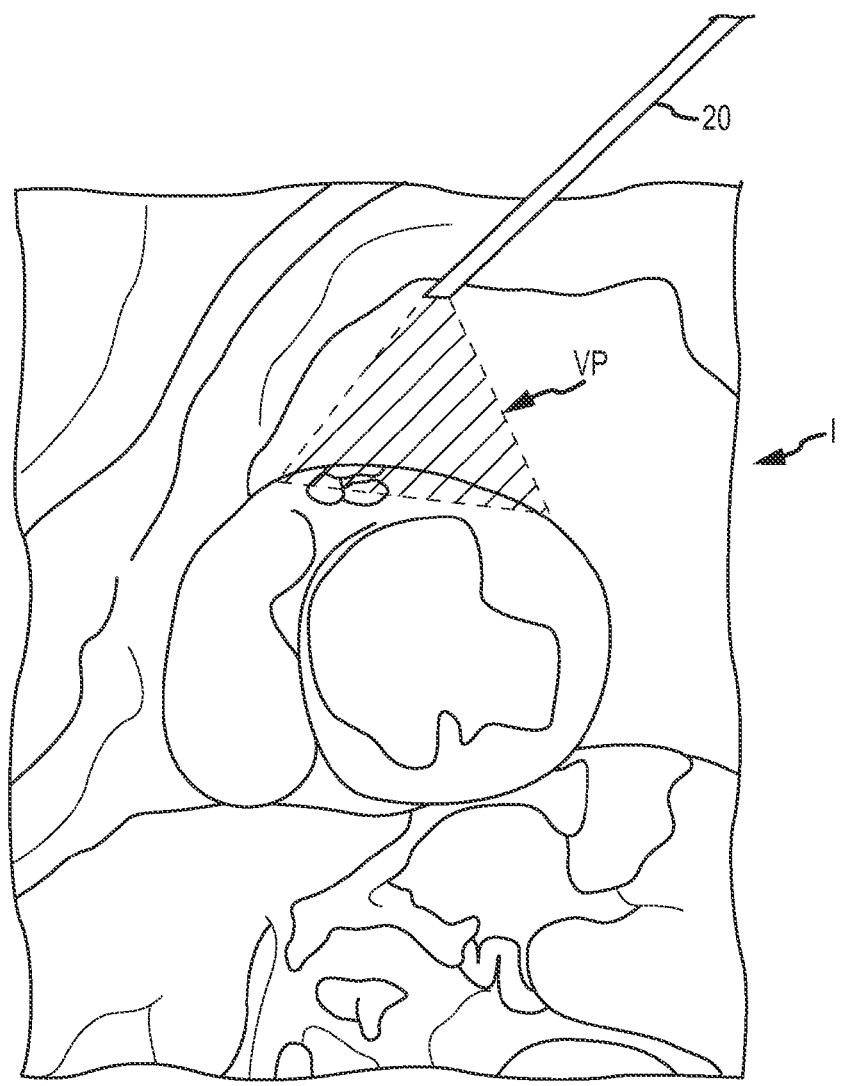

Referring now to FIGS. 2C and 2D an MRI image I taken along viewing plane VP schematically illustrates use of a thoracoscope 20 to provide a field of view encompassing a region of the pericardium of the heart, with the region including a target site for deployment of one or more epicardial anchors of the implant system.

Figure 3A:
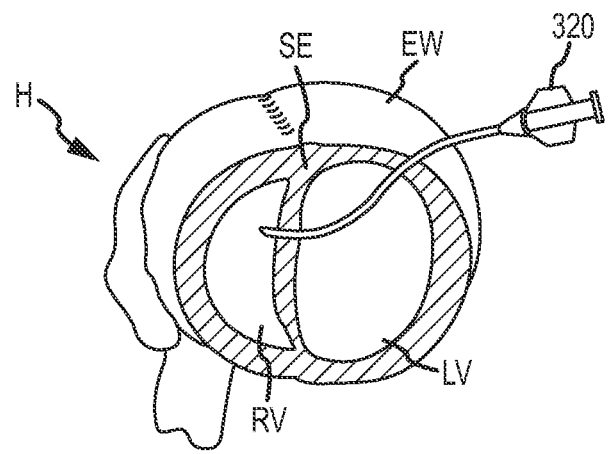
FIGS. 3A-3O illustrate a method of reducing the distance between opposed walls of a heart, according to an embodiment of the invention.
Figure 3B:
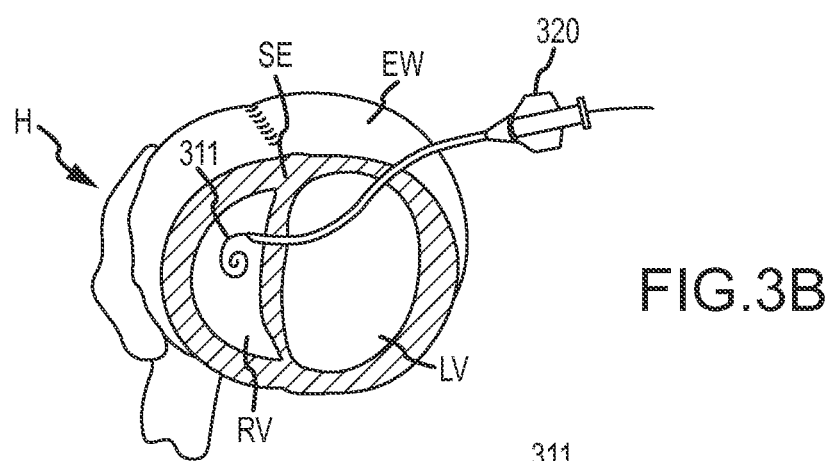
Figure 3C:
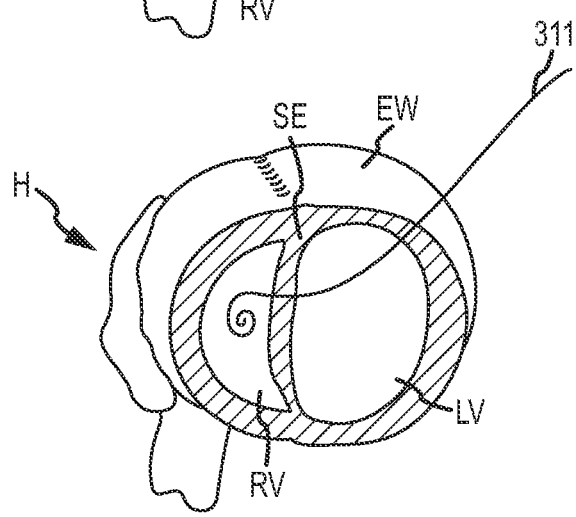
Figure 3D:
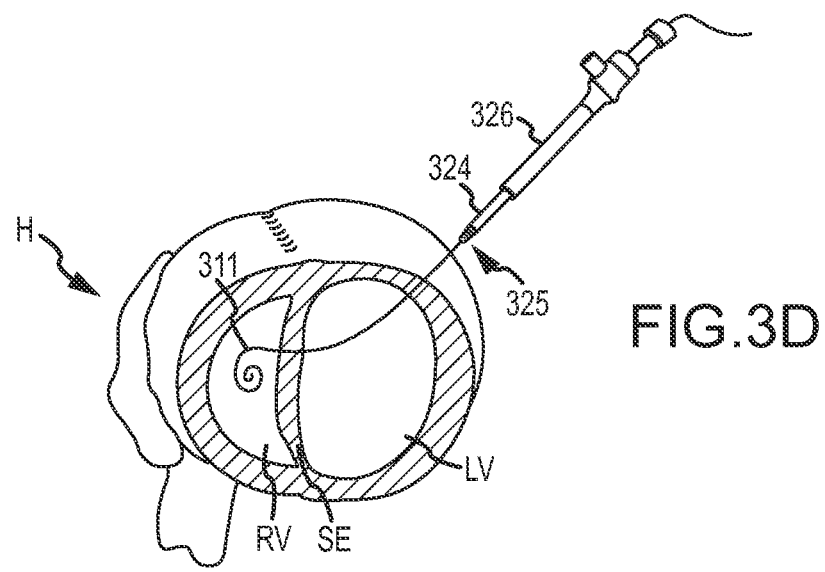
Figure 3E:
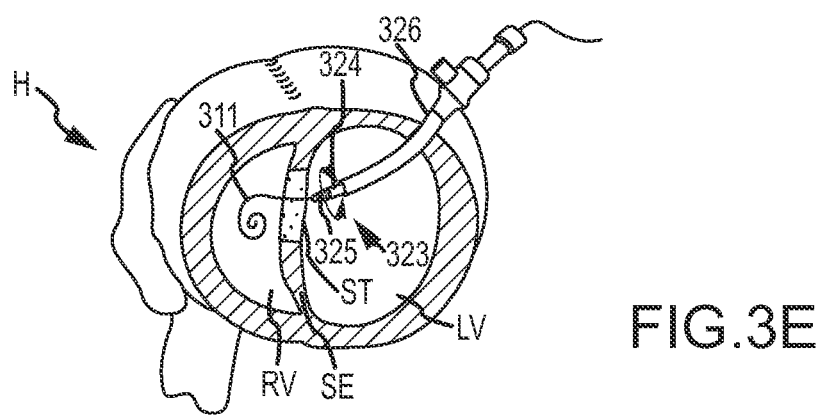
Figure 3F:
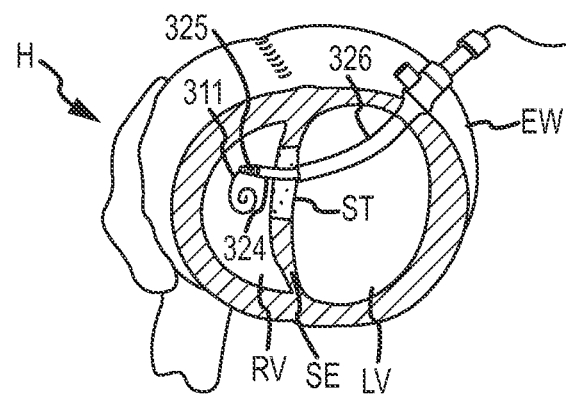
Figure 3G:
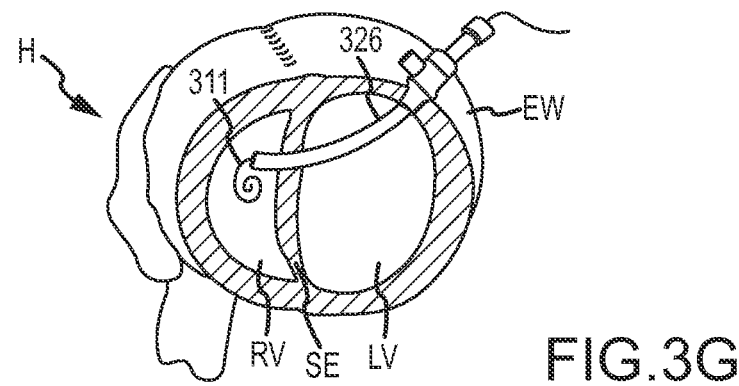
Figure 3H:
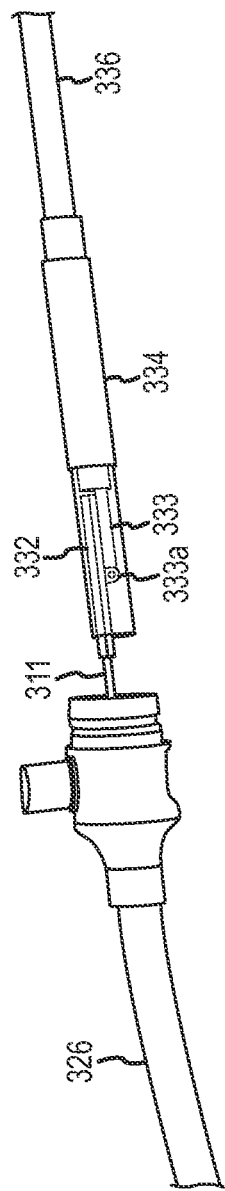
Figure 3I:
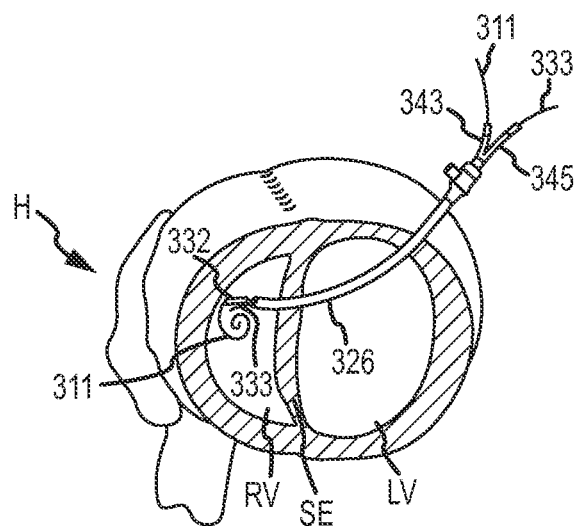
Figure 3J:
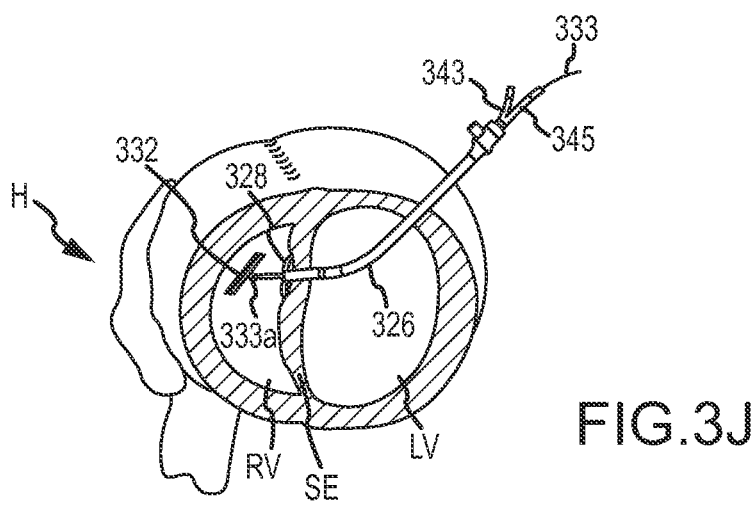
Figure 3K:
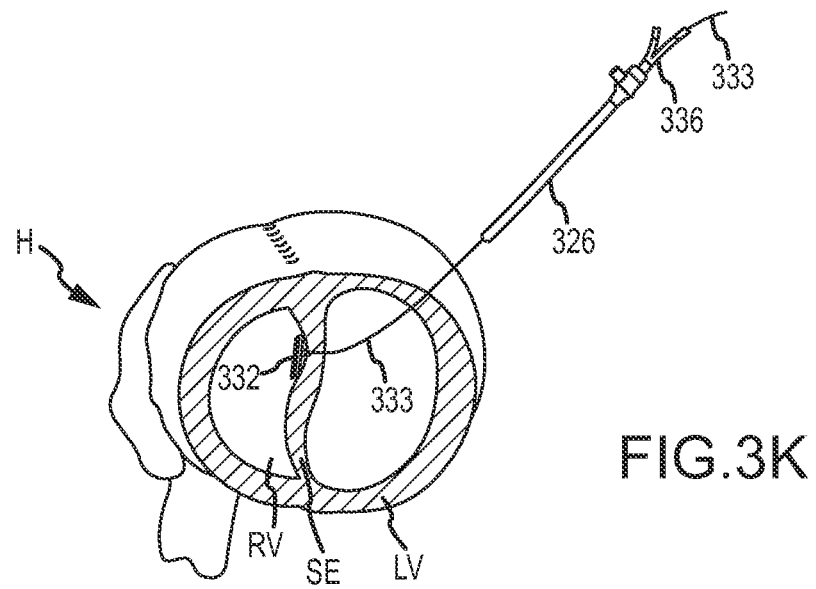
Figure 3L:
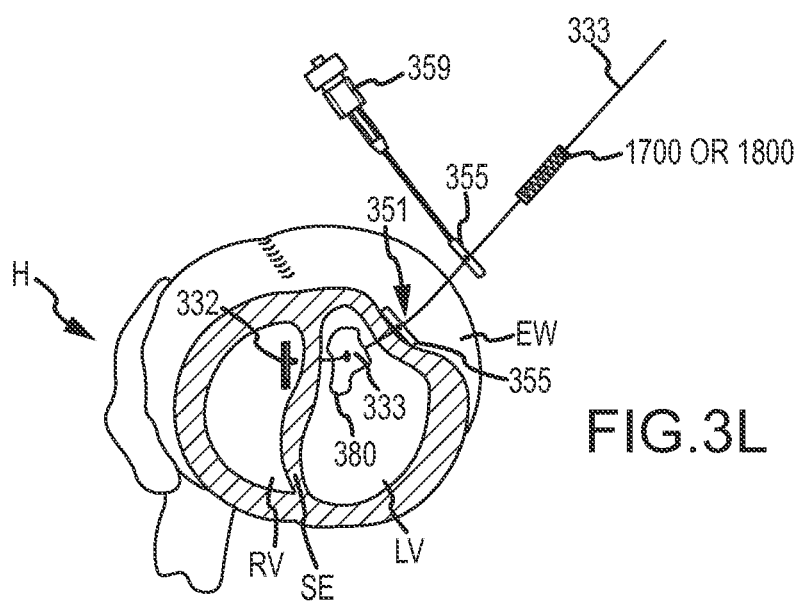
Figure 3M:
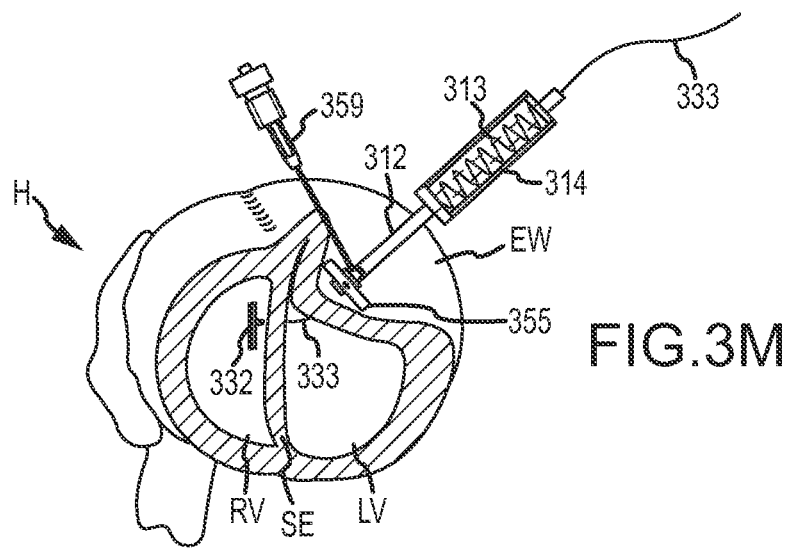
Figure 3N:
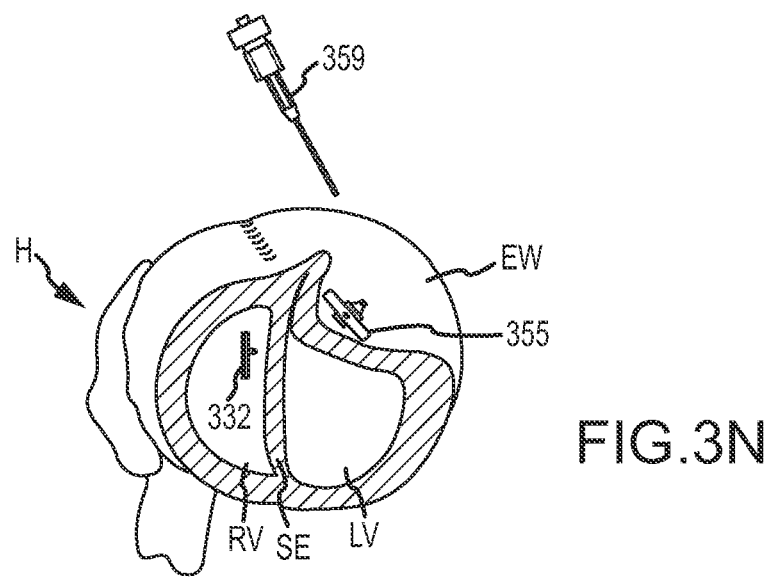
Figure 3O:
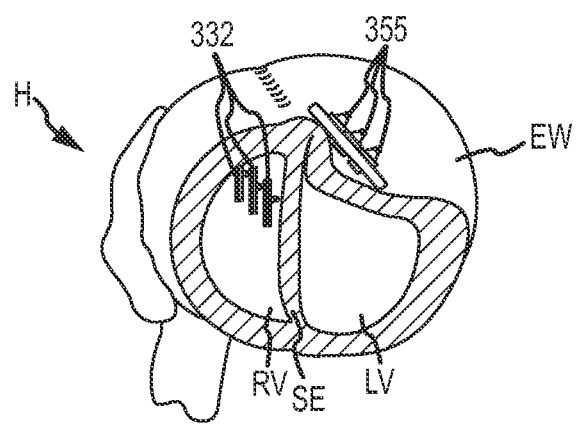

Referring now to FIGS. 3A-3O, shown is a method of reducing the distance between opposed walls of a heart H, and specifically of reducing the distance between the septum SE and the external wall EW of the left ventricle LV. In some embodiments, the method is performed endoscopically, percutaneously, or otherwise in a minimally or less invasive manner. The heart may be accessed through, for example, a small incision made between the ribs or a thoracotomy. As shown in FIG. 3A, a bent insertion needle or guidewire introducer 320 is passed through a desired insertion path through the left ventricle LV wall and through septum SE into the right ventricle RV. Guidewire introducer 320 may be configured so that the perforations made by guidewire introducer 320 on the left ventricular wall and the septum wall are perpendicular to their respective walls. As shown in FIG. 3B, a guidewire 311 is placed through the lumen of guidewire introducer 320 so that guidewire 311 threads through the outer left ventricle LV wall, through the septum SE, and into the right ventricle RV. Guidewire 311 may be inserted along and may define an epicardial access path, which may be an arcuate path. As shown in FIG. 3C, guidewire introducer 320 is removed from the heart leaving guidewire 311 threaded through the external wall EW, left ventricle LV, and septum SE into right ventricle RV. Examples of bent insertion needle or guidewire introducer 320 may be found in US Patent Publication No. US2010/0016655 that is incorporated herein by reference as described previously.

Figure 10:
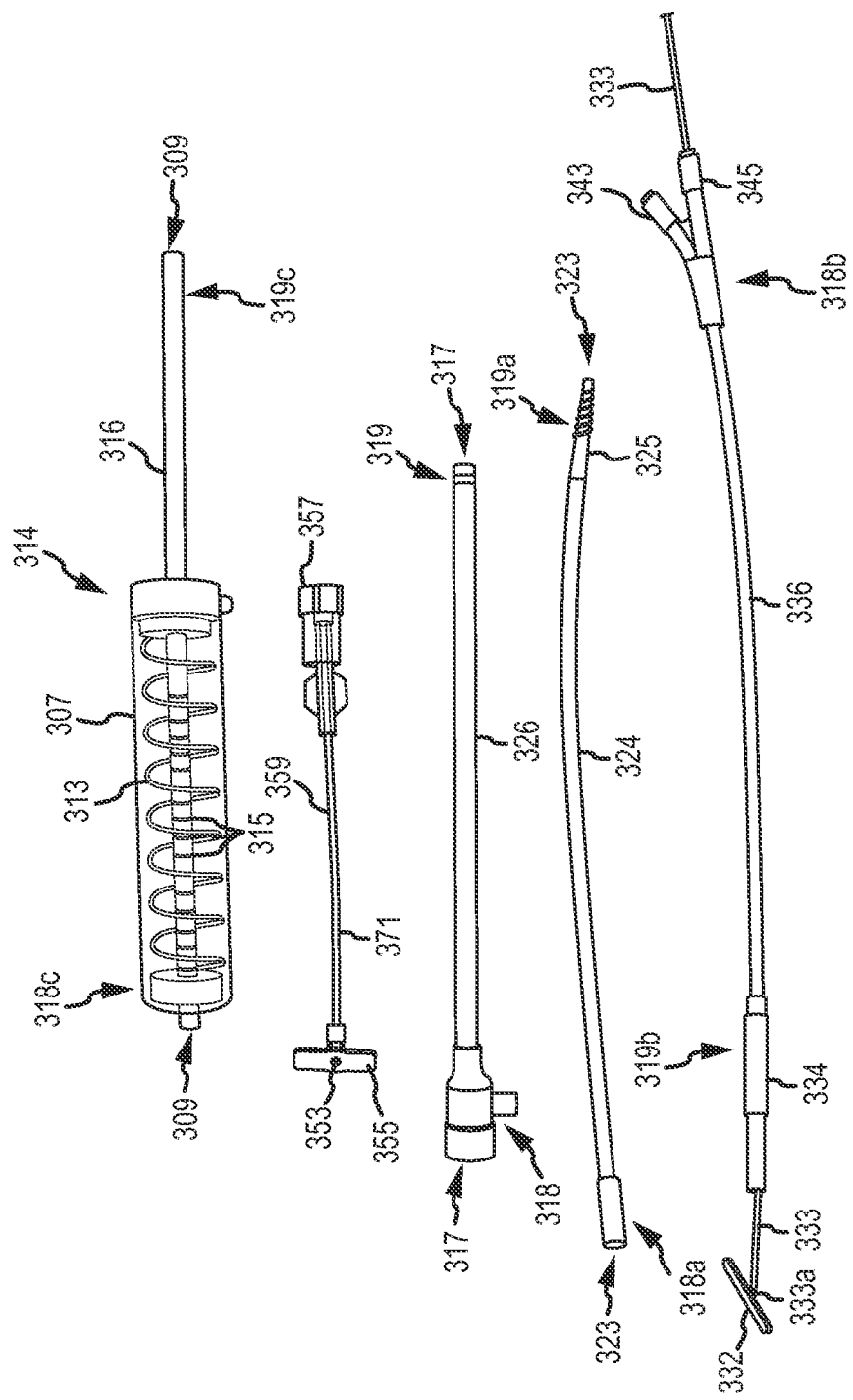
FIGS. 10-10F illustrates components of an over-the-wire implant delivery system and their use, according to an embodiment of the invention.

FIG. 3D shows a dilating catheter 324 inserted within a lumen of a delivery catheter 326 with the dilating catheter 324 and delivery catheter 326 being advanced over the guidewire 311 to external wall EW of heart H. Delivery catheter 326 may include a hemostasis valve at a proximal end outside the heart to minimize blood loss from the patient. Guidewire 311 is inserted through a lumen of dilating catheter 324. Additional aspects of dilating catheter 324 and delivery catheter 326 are shown in FIG. 10. In other embodiments, such as the embodiments illustrated in FIGS. 11A-11C the delivery catheter and dilating catheter may be combined into a single catheter device.

FIG. 3E shows the dilating catheter 324 and delivery catheter 326 inserted over guidewire 311 through the external wall EW and into left ventricle LV so that the distal tip of dilating catheter 324 is proximate septum SE. Dilating catheter 324 and delivery catheter 326 may comprise a flexible material so as to curve or bend along the arcuate epicardial access path defined by guidewire 311.

Dilating catheter 324 may dilate or enlarge an aperture in septum SE and/or external wall EW formed from inserting guidewire introducer 320 through septum SE and/or external wall EW. To dilate the aperture through septum SE and/or external wall EW, dilating catheter 324 includes a dilating feature at the distal tip. For example, in some embodiments, dilating catheter 324 comprises a tapering threaded tip 325 as shown in more detail in FIG. 10. Dilating catheter 324 may be rotated 323 about an axis as dilating catheter 324 is inserted through septum SE and/or external wall EW to dilate the aperture. The threaded surface of tapering threaded tip 325 contacts tissue of the septum SE and/or external wall EW and cuts the tissue, compresses the tissue, or otherwise widens the aperture. The tapered threaded tip 325 reduces the amount of axial pressure that is otherwise applied to septum SE and/or external wall EW as a delivery catheter is inserted therethrough, which may reduce arrhythmia or other conditions resulting from axial pressure exerted on the septum SE and/or external wall EW. In other words, rotation of tapering threaded tip 325 may help advance delivery catheter 326 with less axial force than would otherwise be used to axially advance a tapered catheter, and may limit axial force to the septum sufficiently to inhibit arrhythmia of the heart. The tissue contacted by the tapered threaded tip 325 may include scar tissue ST, which generally is tough or otherwise difficult to penetrate and which, therefore, requires an appreciable amount of axial force to penetrate. Dilating catheter 324 and/or delivery catheter 326 may be formed of a flexible material so that dilating catheter 324 may be rotated while being bent along the arcuate epicardial access path of guidewire 311. Put another way, rotation of dilating catheter 324 may be transmitted axially over guidewire 311 around the arcuate epicardial access path. Dilating catheter 324 may alternatively include a cutting element instead of or in addition to tapered threaded tip 325. The cutting element may use RF energy (e.g., an RF transceptal needle) to cut through the tissue of the septum SE and/or external wall EW. Such RF devices are described herein. Likewise, delivery catheter 326 and/or dilating catheter 324 may be steerable catheters so that a distal end of catheters, 324 and/or 326, may be positioned virtually anywhere within right ventricle (e.g., near the pulmonary artery and the like).

Figure 10A:
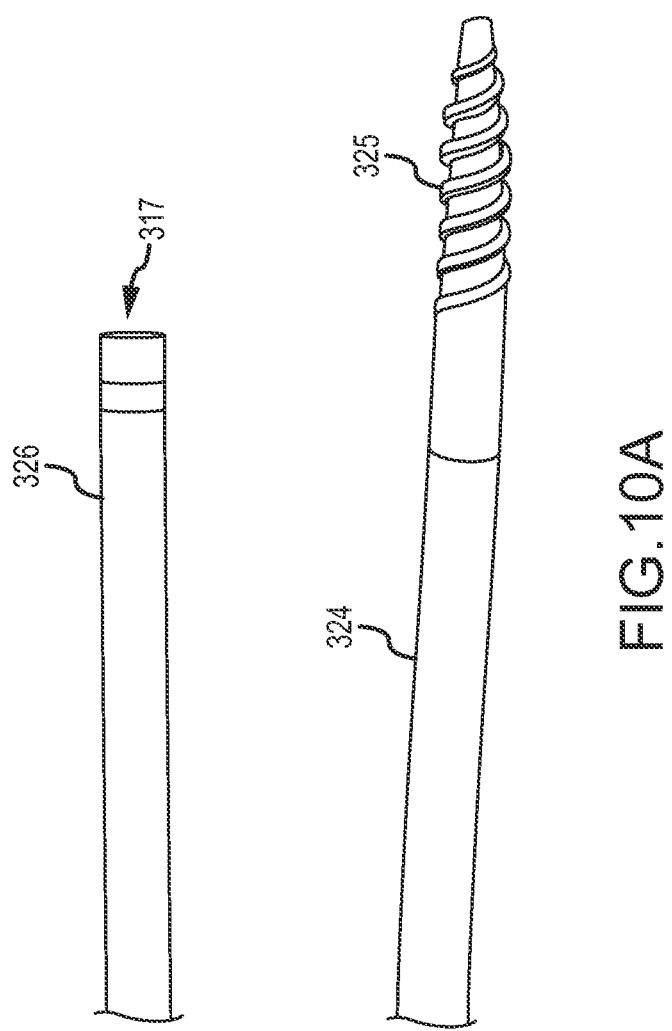
FIGS. 10G-10I illustrate an exemplary axially flexible helical screw-tip dilator and its use for traversing a wall of the heart, according to an embodiment of the invention.
Figure 10B:
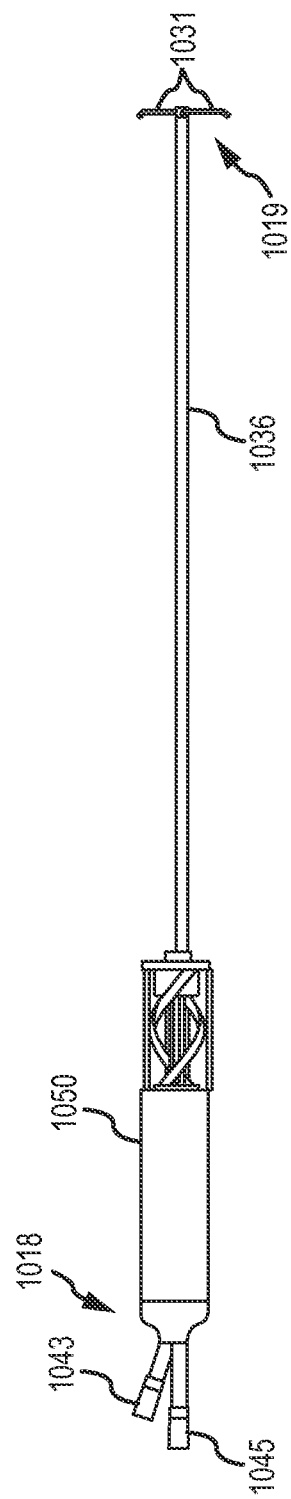
Figure 10E:
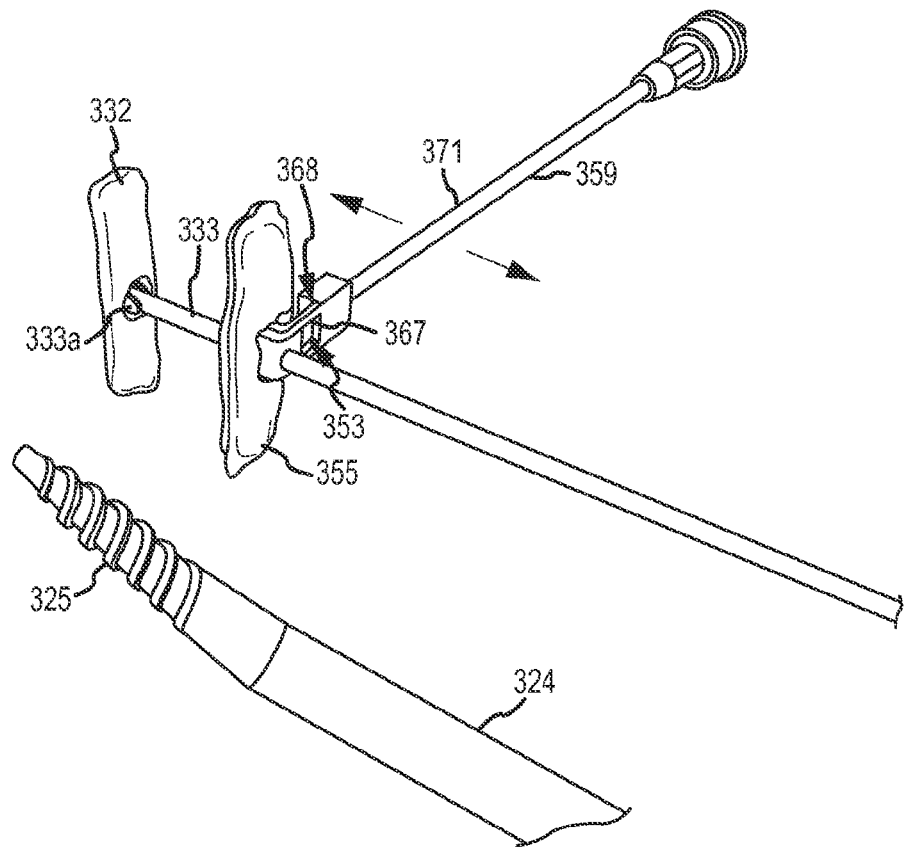
Figure 10F:
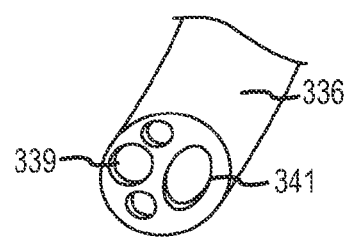
Figure 10I:
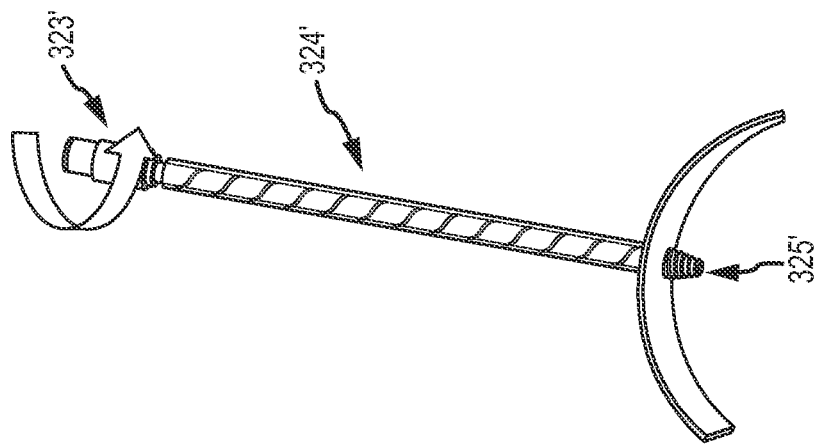
Figure 10H:
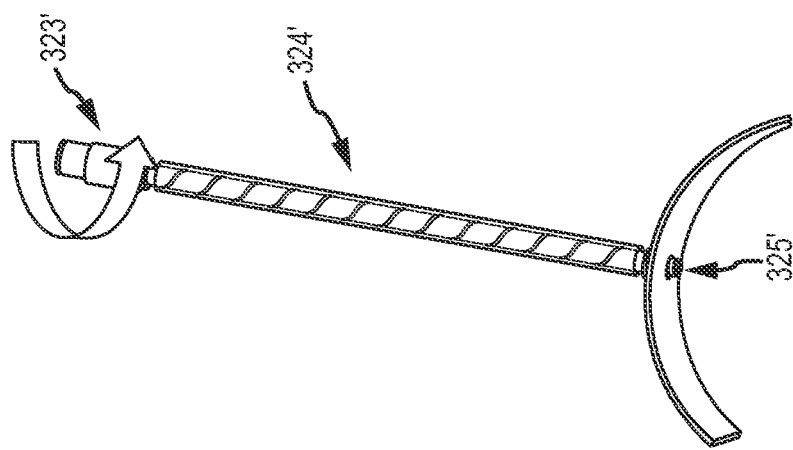
Figure 10G:
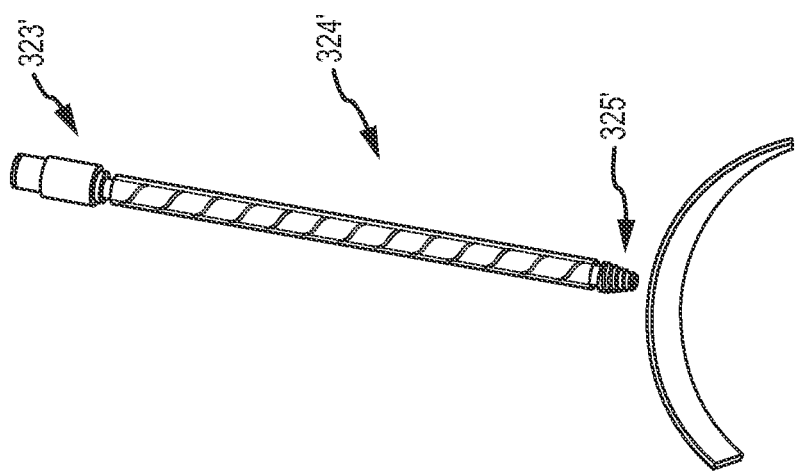

FIGS. 10G-10I illustrate an alternative embodiment of a dilation catheter 324' having a tapered threaded tip 325'. In this embodiment, tapered threaded tip 325' is configured to rotationally advance or screw into and through tissue of external wall EW and/or septum SE. Dilation catheter 324' includes inner and outer concentric shafts that extend proximally of tapered threaded tip 325' toward a proximal hub 323'. The shafts are laterally flexible to accommodate curvature of the axis of the dilation catheter, and the hub 323' and tapered threaded tip 325' may be axially coupled to the inner shaft and the inner shaft may be sufficiently axially stiff so that rotation of the hub 323' outside the body induces controlled rotation of the tapered threaded tip 325' into and through the tissue of external wall EW and/or septum SE while the outer shaft remains rotationally stationary.

FIG. 3F shows the dilating catheter 324 and delivery catheter 324 advanced along the arcuate epicardial access path over guidewire 311 through septum wall SE and into right ventricle RV after dilating catheter 324 has dilated or expanded the aperture through septum SE and/or external wall EW, which, as described previously, may involve contacting and/or cutting scar tissue ST. FIG. 3G shows the dilating catheter 324 removed from the lumen of deliver catheter 326 so that delivery catheter 326 remains within right ventricle RV and inserted through septum SE and external wall EW.

FIG. 3H shows septal anchor 332 being inserted within a proximal end of delivery catheter 326. Septal anchor 332 is positioned within loading cartridge 334 that fits at a distal end within the hemostasis valve of delivery catheter 326 and that couples at a proximal end with pusher tube 336. Loading cartridge 334 facilitates insertion of septal anchor 332 and pusher tube 336 within delivery catheter 326. Additional aspects of septal anchor 332, loading cartridge 334, and pusher tube 336 are shown in FIG. 10. Septal anchor 332 is rotatably coupled with tether or tension member 333 at pivot point 333a. Septal anchor 332 includes a lumen through which guidewire 311 is inserted so that septal anchor 332 is advancable over the guidewire. The lumen of septal anchor 332 may extend along an axis of the septal anchor 332. The lumen may slidably receive guidewire 311 therein so as to accommodate advancement of septal anchor 332 into heart H by advancing septal anchor 332 axially over guidewire 311 and into the right ventricle RV. Guidewire 311 may help control a position of septal anchor 332 and inhibit injury to tissue structures along or within the heart H, right ventricle RV, and/or left ventricle LV, such as valve leaflets, chordae, papillary muscles, and the like.

Similarly, pusher tube 336 includes a guidewire lumen (e.g., guidewire lumen 339 shown in FIG. 10F), through which guidewire 311 may be inserted. When guidewire 311 is inserted through the lumen of septal anchor 332 and pusher tube 336, guidewire 311 orients septal anchor 332 in a fixed orientation (i.e., a low profile configuration) and axially aligns the lumens of septal anchor 332 and pusher tube 336. The low profile configuration allows septal anchor 332 to be easily inserted within and pushed through the lumen of delivery catheter 326. Pusher tube 336 also includes a tether lumen, (e.g., tether lumen 341 shown in FIG. 10F), through which tether 333 is inserted.

FIG. 3I illustrates septal anchor 332 advanced through delivery catheter 326 via pusher tube 336 into the right ventricle RV of heart H over guidewire 311. Guidewire 311 maintains septal anchor 332 in the axially aligned relationship with pusher tube 336 and tether 333. FIG. 3I also shows the guidewire 311 exiting pusher tube 336 via guidewire port 343 and shows tether 333 exiting pusher tube 336 via tether port 345. Additional aspect of guidewire port 343 and tether port 345 are shown in FIG. 10. Because septal anchor 332 is guided into the right ventricle RV over guidewire 311, septal anchor 332 may be positioned virtually anywhere guidewire 311 is positioned, such near the pulmonary artery and the like. Such positionability of septal anchor 332 allows sensitive heart tissues, such as valve leaflets, chordae, papillary muscles, and the like, to be avoided or contact therewith minimized. Further, positioning septal anchor 332 over guidewire 311 minimizes entanglement with and/or contact between septal anchor 332 and sensitive heart tissues, such as valve leaflets, chordae, papillary muscles, and the like, because septal anchor 332 is fixed in relation to tether 333 and pusher tube 336 and not able to freely rotate and entangle with or contact such features of heart H.

Septal anchor 332 may optionally be advanced into and/or within heart H by pushing the anchor distally using a flexible compressive shaft of pusher tube 336, 1036, or the like. In either case, the compressive shaft being used as a pusher catheter may have separate lumens for guidewire 311 and tether 333 as shown, with both lumens extending between the distal end and the proximal end of the catheter body. More than 2 lumens may also be provided, and the multi-lumen structure can enhance rotational control over septal anchor 332 about the axis of tether 333, and/or may facilitate orienting the arms of septal anchor 332 by rotation of the pusher tube 336/1036 (optionally along with tether 333 and guidewire 311 therein) from outside the patient. In some embodiments, tether 333 may have an elongate cross-section and tether lumen 341/1041 may have a corresponding elongate cross-section so as to enhance rotational control over the advanced septal anchor 332 after guidewire 311 is pulled free of septal anchor 332, as can be understood with reference to the distal end of pusher tube 1036 shown in FIG. 10C, and with reference to the elongate cross-section of the large tether lumen 341 of pusher catheter 336 shown in FIG. 10F. In some embodiments, one of the unnumbered lumens on either side of guidewire lumen 339 may receive guidewire 311.

Figure 12A:
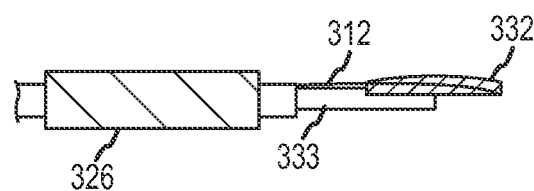
FIGS. 12A and 12B schematically illustrate an anchor repositioning leash and its use, according to an embodiment of the invention.
Figure 12B:
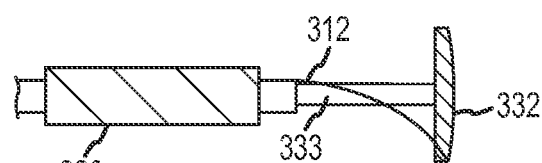
Figure 13C:
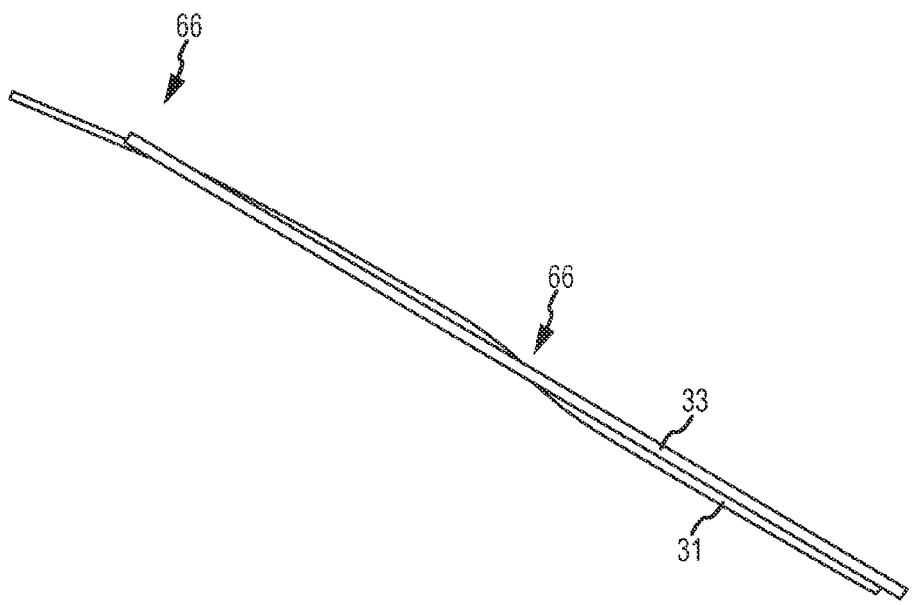
Figure 14A:
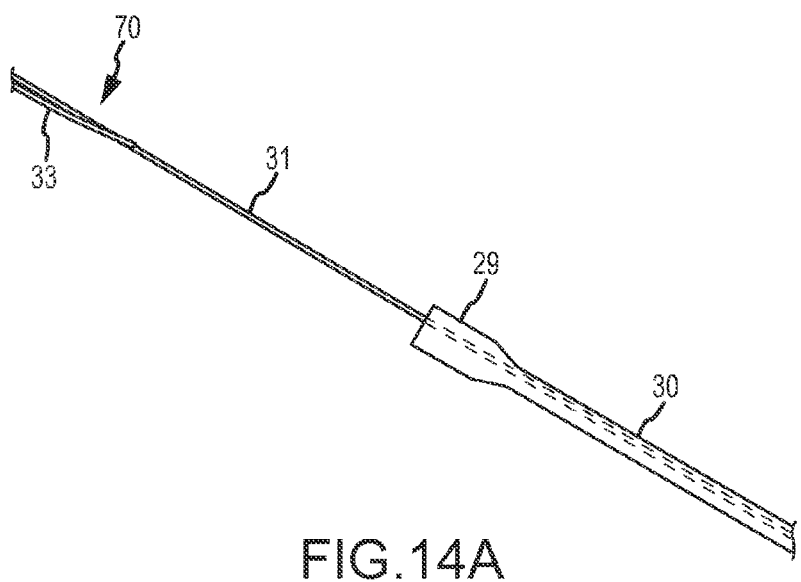
FIGS. 14A-14C schematically illustrate advancing the tension member and anchor along a right ventricle access tool over a guidewire, and out from the access tool and through the septum and an external wall of the left ventricle, according to an embodiment of the invention.
Figure 14B:
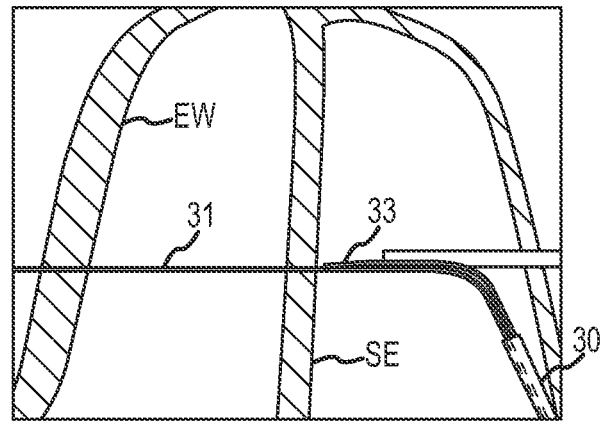
Figure 14C:
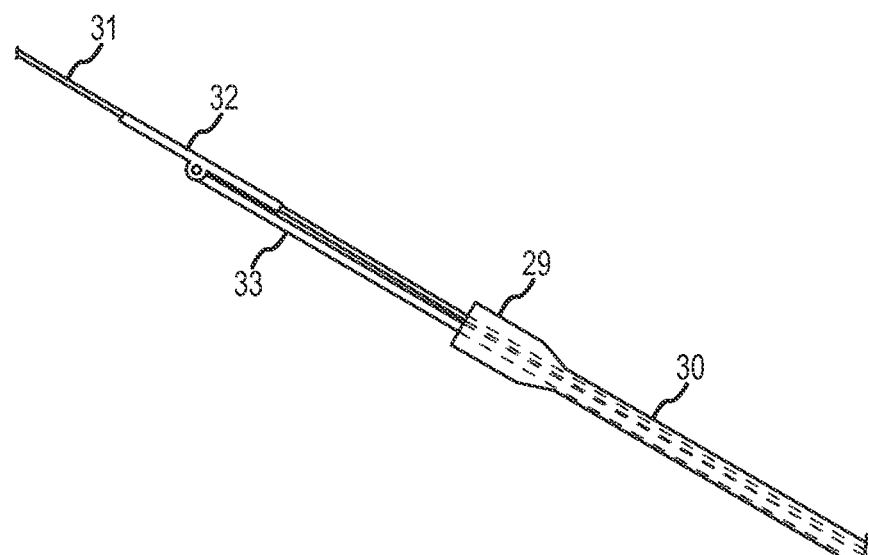
Figure 16A:
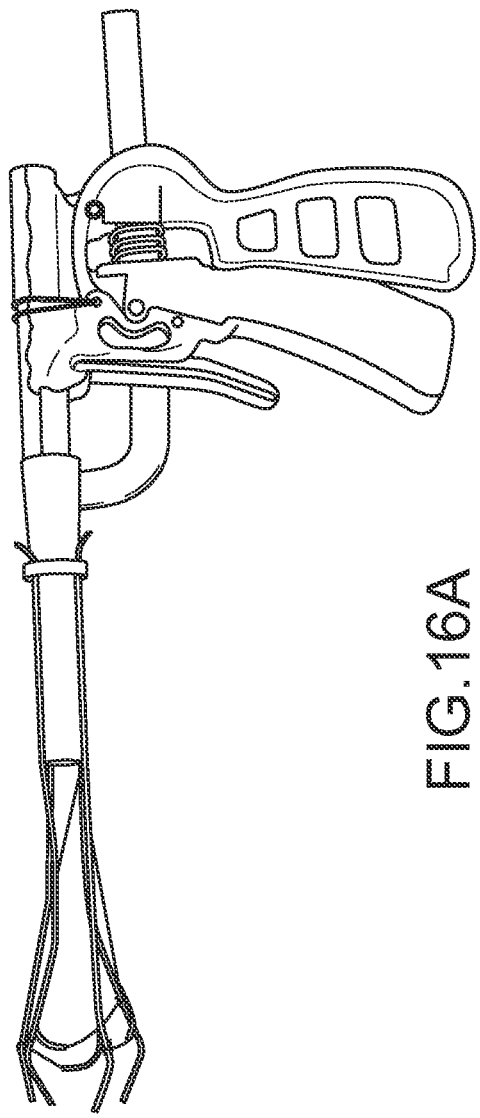
FIGS. 16A-16D illustrate an epicardial hemostasis tool having a working lumen to provide access through a tissue tract to a epicardium about an epicardial access path, wherein the tool is configured to compress the external wall of the heart toward the access path so as to provide hemostasis, according to an embodiment of the invention.
Figure 16B:
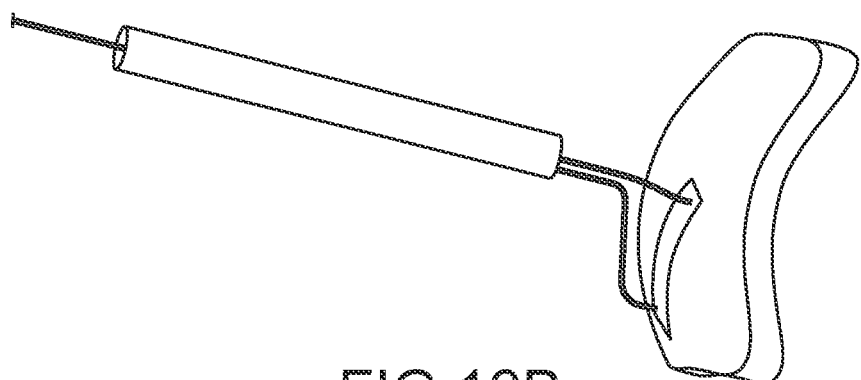
Figure 16C:
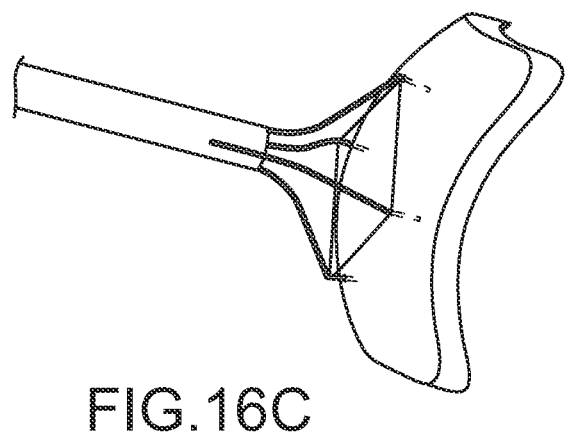
Figure 16D:
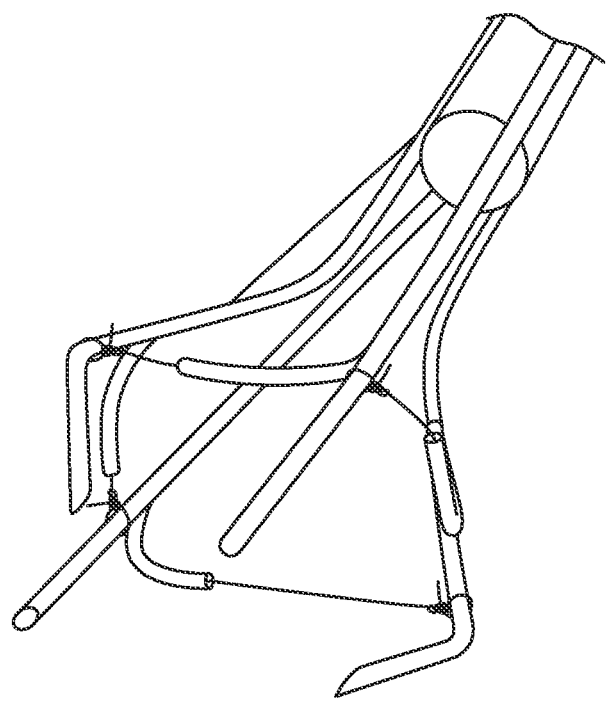

FIG. 3J shows guidewire 311 being removed from the right ventricle via guidewire port 343 and from the guidewire lumen of septal anchor 332. Removal of guidewire 311 from the guidewire lumen of septal anchor 332 allows septal anchor 332 to pivot about pivot point 333a so that septal anchor 332 is rotatable relative to tether 333. Control over the pivoting of septal anchor 332 may be provided by using leash 312 as shown in FIGS. 12A-12B. For example, once septal anchor 332 is disposed within right ventricle RV and beyond delivery catheter 326, guidewire 311 can be removed and septal anchor 332 positioned transverse to tether 333 by engagement between septal anchor 332 and the surface of septum SE, or by pulling on leash 312 extending through catheter 326 or pusher tube 336. Radial positioning of septal anchor 332 can be provided by rotating the end of tether 333, which remains outside the patient.

FIG. 3J further shows a laterally deployable member 328, such as deployable arms 1031 of pusher tube 1036 of FIGS. 10B-10C, deployed from the distal end of pusher tube 336 so as to stabilize the pusher tube 336 and delivery catheter 326 relative to the beating heart tissue around left ventricle LV. Suitable deployable members 328 may include a malecot, a pair of opposed deployable arms (optionally similar to those described below with reference to FIGS. 10B and 10C), a balloon, or the like. Laterally deployable member 328 may be configured for engagement against an interior surface of the left ventricle LV or against the epicardial surface of the left ventricle (such as by having the deployable structure spaced proximally of the distal end). Laterally deployable member 328 may be used to urge septum SE toward external wall EW and thereby provide additional space within right ventricle RV for the deployment of septal anchor 332 and/or may facilitate tensioning of septal anchor 332 and an epicardial anchor to reshape heart H. Some embodiments do not involve laterally deployable member 328 and septal anchor 332 is deployed directly within the space of right ventricle RV. Deployable members 328 may be deployed within right ventricle RV before or after guidewire 311 is removed and septal anchor 332 released from the fixed orientation.

FIG. 3K shows delivery catheter 326 and pusher tube 336 being removed from the right ventricle RV of heart H so that septal anchor 332 is positioned against the surface of the wall of septum SE. Tether 333 extends from septal anchor 332 through the aperture in septum SE and external wall EW to the exterior of heart H. Tension may be applied to tension member 333 to urge septum SE toward external wall EW. FIG. 3L shows an epicardial anchor 355 coupled with tension member 333 and being advanced toward external wall EW via anchor set tool 359. Epicardial anchor 355 includes a lumen 353 (shown in FIGS. 10, 10D, 10E, and 15A-15D), through which tether 333 is inserted. Epicardial anchor 355 has a spring cam structure 363 as more fully shown in FIGS. 15A-15D and described in US Patent Publication No. US2010/0016655, as published on Jan. 21, 2010 and entitled "Cardiac Anchor Structures, Methods, and Systems for treatment of Congestive Heart Failure and Other Conditions;" the full disclosures of which are incorporated herein by reference. The spring cam 363 allows epicardial anchor 355 to slide along tether 333 toward septal anchor 332, but inhibits sliding of epicardial anchor 355 away from septal anchor 332, so that the spring cam 363 effectively maintains a tissue engagement force between the anchors. This set-force interaction between tether 333 and epicardial anchor 355 is advantageous once the proper force is applied, but it can be challenging to apply the desired force when the heart is beating. To more accurately apply septal/external wall engagement forces within a desired range, anchor set tool 359 can engage the cam spring mechanism 363 of epicardial anchor 355 so as to allow the anchor to slide both axial directions along tether 333 (shown in FIG. 10E), thereby configuring epicardial anchor 355 into a variable force mode. This allows a controlled force to be applied between the tether 333 and epicardial anchor 355 despite beating of the heart, with the force preferably being applied by a force application tool 314 having an elongate shaft 316 as described in FIG. 3M.

The applied anchor force may be an appropriate amount of force to bring external wall EW and septum SE into engagement while preventing migration of epicardial anchor 355 and septal anchor 332 relative to external wall EW and septum SE, respectively. For example, the force may be sufficient so that an inner surface of external wall EW and septum SE directly contact each other and so that epicardial anchor 355 and septal anchor 332 are secured tightly about external wall EW and septum SE, respectively, but not too strong to cause epicardial anchor 355 and/or septal anchor 332 to be pulled through and/or into external wall EW and/or septum SE.

The appropriate anchor force to sufficiently secure the anchors about the heart walls while preventing migration may fall within a range of forces, which may vary from patient to patient. For example, contraction of a patient's heart typically induces a Ventricular Contractile Force (VCF) on the tether and/or anchors. The VCF applied generally depends on the patient's blood pressure, heart size, and the like, and thus, may vary from patient to patient. In some embodiments, an anchor force may be applied to the anchors beyond the VCF that is naturally placed on the anchors and tether due to heart contraction. As such, the total force applied to the anchors (i.e., the VCF+anchor force) may vary from patient to patient. While the VCF and total force applied may vary from patient to patient, however, it may be desirable to apply an anchor force within a desired range that minimizes anchor migration, pull through, tissue necrosis, and the like.

As described in more detail in the experimental section below, an anchor force range of between about 2N (i.e., 2 Newtons) and about 8N beyond the VCF has been demonstrated to effectively close opposing portions of a heart and improve performance of the heart while minimizing anchor migration, pull through, tissue necrosis, and other unwanted effects. In some embodiments, it may be desirable to apply an anchor force between a range of about 2N and 8N beyond the VCF, between 2N and 6N beyond the VCF, between about 3N and 4N beyond the VCF, and the like. As described in the experimental section, such forces were found to be sufficient enough to prevent migration of the anchors without causing the anchors to be pulled through the external wall EW and/or septum SE. Such forces were also found to minimize necrosis of the tissue of external wall EW and/or septum SE surrounding the anchors.

Further, as also described in the experimental section below, it may be desirable to ensure that the internal and external anchors have roughly the same dimensions or cross section areas. For example, it has been demonstrated that when the internal and external anchors are sized differently or have different cross sectional areas, such as where the external anchor is wider than the internal anchor, the force on one of the heart walls may be increased. For example, if the internal anchor has a smaller width than the external anchor, the tension on an edge of the internal anchor may be increased. The increased edge tension on the internal or external anchor may result in unwanted anchor migration, pull through, and/or tissue necrosis. In contrast, when the anchors have roughly the same dimensions or "footprint", the force may be distributed on the heart walls in a relatively even manner, which inhibits migration of either or both anchors through the tissue.

The force application tool 314 may provide an indication (e.g., via indicia 315) of the force applied so that a force within the desired force range may be applied to the anchors.

Further, force application tool 314 and/or epicardial anchor 355 may be configured to apply the appropriate force while the heart is beating. For example, the variable force mode of epicardial anchor 355, allowing proximal and distal movement of epicardial anchor 355 about tether 333, and/or a spring mechanism 313 of force application tool 314 may allow epicardial anchor 355 and force application tool 314 to compensate for movement of heart H as the heart beats and as the desired anchor force is applied to ensure that too little or too much force is not applied. Force application tool 314 may also be configured so that the applied anchor force cannot exceed a predetermined value. For example, force application tool 314 may be configured so that an operator of force application tool 314 cannot apply an anchor force greater than 6N, or in some embodiments, greater than 4N. In this manner, necrosis of heart tissue, migration of the anchors, pulling of the anchors through the heart tissue, and/or other potential problems associated with excessive or insufficient anchor forces may be minimized or eliminated.

The force application tool 314 may also be used to effectively apply the anchor force between the above ranges beyond the VCF. According to one embodiment, the force application tool 314 may be set in a "locked" position so that the shaft 316 is locked in place and the force application tool 314 functions as a rigid or semi-rigid tool. In this configuration, the force application tool 314 may press against the epicardial anchor 355 to bring the walls of the heart together. When the walls of the heart are brought together, the force exerted by the heart on the walls and force application tool 314 may be less variable. Stated differently, with the application tool 314 in the rigid or semi-rigid configuration, the VCF may be overcome to bring the walls of the heart together. The force application tool 314 may then be unlocked and a force indicator (i.e., indicia 315) normalized or zeroed to account for the VCF. With the force indicator normalized, the force application tool 314 may be used to apply the additional anchor force to the desired amount (e.g., between 2-8N, 2-6N, 3-4N, and the like). The normalized or zeroed force indicator may appropriately indicate or display the anchor force applied. In this manner, a patient's VCF may be account for and a desired anchor force that closes the heart walls while minimizing unwanted effects may be applied beyond the VCF.

In some embodiments, the force application tool 314 may be retracted slightly after the heart walls are brought together to ensure that no additional force, or only a minor force, is applied to the epicardial anchor 355 before the force indicator is normalized. In other embodiments, thoracoscopic guidance, echo guidance, and the like, may be used to determine when the force application tool 314 brings the heart walls together or close together. At this point the force application tool 314 may be normalized and the VCF accounted for.

As shown in greater detail in FIGS. 10D, 10E, and 15A-15D, to engage the cam spring mechanism 363 of epicardial anchor 355, anchor set tool 359 may include a pair of hooks 368 that are positionable around a pair of arms 364 that are in turn connected to cam spring mechanism 363 or otherwise operational therewith. A retractable rod 367 may be positioned between the pair of hooks 368. Rod 367 may be retracted within a sheath 371 or extended therefrom upon actuation of a retracting device, such as a rotatable cap 357. In operation, the pair of hooks 368 may be clamped around arms 364 so that housing 365 is positioned between hooks 368. Retracting device (e.g., rotatable cap 357) is then operated so that rod 367 extends from sheath 371 and contacts housing surface 366. Further operation of retracting device (e.g., rotatable cap 357) forces rod 367 to push on housing surface 366, which causes hooks 368 to pull on arms 364, which in turn causes cam spring mechanism 363 to rotate so that the cam rotates away from contact with tether 333 thereby permitting epicardial anchor 355 to slide both toward and away from septal anchor 332. Similarly, retracting device (e.g., rotatable cap 357) may be operated in a reverse manner so that rod 367 is retracted within sheath 371 and arms 364 resiliently return to a position in which the cam rotates to contact tether 333 thereby inhibiting epicardial anchor 355 from sliding away from septal anchor 332. Arms 364 may act as a spring to bias the cam toward tether 333 and lock epicardial anchor 355 about tether 333. The retracting device (e.g., rotatable cap 357) may be operated from outside the patient body so as to lock/reconfigure epicardial anchor 355 in the set force mode or unlock/reconfigure epicardial anchor 255 in the variable force mode.

Figure 18:
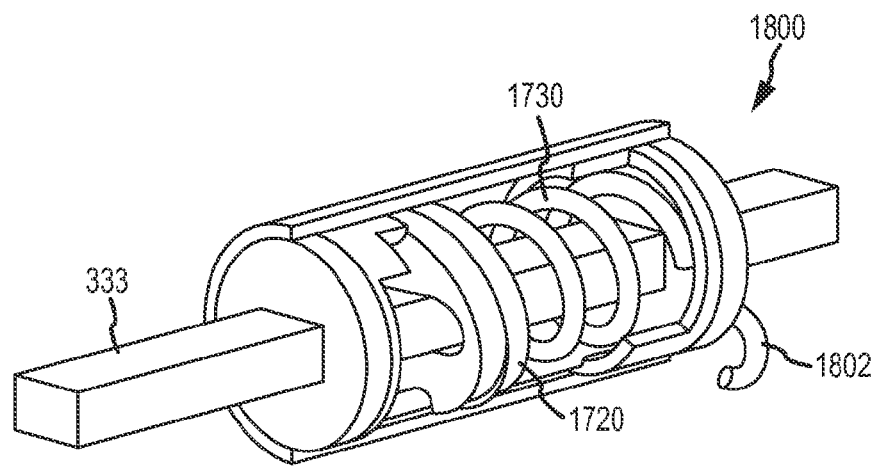
Figure 18A:
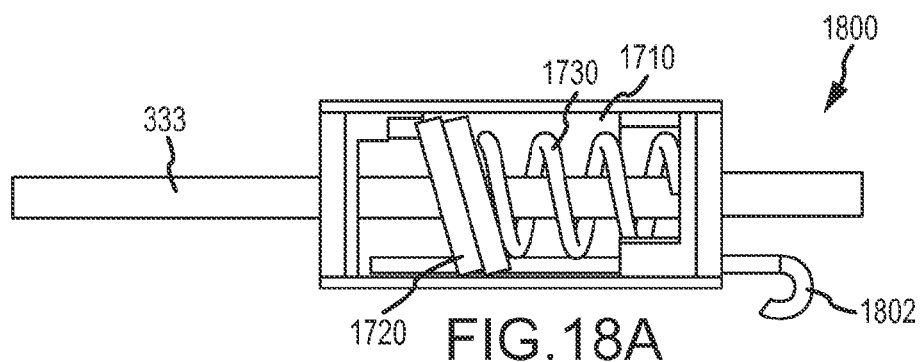
Figure 18B:
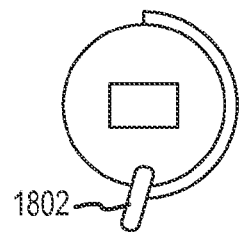

Alternative embodiments of an epicardial anchor structure, 1700 and 1800, are shown in FIGS. 17-18B. Epicardial anchor structures, 1700 and 1800, can be advanced axially through a working lumen (optionally through a working lumen of the epicardial hemostasis device described herein) and can also be reconfigured between a set-force mode and a variable-force mode through the access lumen. Epicardial anchor structures, 1700 and 1800, may include a lock plate 1720 or a pair of lock plates within lumen body 1710. The lock plate or plates 1720 may include an aperture through which tether 333 is inserted. Lock plates 1720 may be biased toward a distal end of epicardial anchor structures, 1700 and 1800, via a spring 1730 disposed within lumen body 1710. Locking plates 1720 may pivot within lumen body 1710 to assume a lock position and grip tether 333 and thereby lock epicardial anchor structures, 1700 and 1800, about tether 333 to prevent proximal movement of the anchors relative to tether 333. Locking plates 1720 may also pivot within body lumen 1710 to assume an unlock position and disengage tether 333 and thereby allow epicardial anchor structures, 1700 and 1800, to move distally and proximally relative to tether 333. Spring 1730 may bias locking plates 1720 toward the lock position. For example, the aperture of lock plates 1720 may have a shape corresponding to tether 333 and may be sized slightly larger than tether 333. In the unlock position, lock plates 1720 may assume a vertical position within lumen body 1710, or put another way, lock plates may have a substantially perpendicular orientation with respect to tether 333. Because the aperture of lock plates 1720 corresponds in shape to tether 333 and is sized slightly larger, tether 333 is able to freely pass through the aperture. In the lock position, lock plates 1720 may assume an angled orientation with respect to tether 333, which causes the aperture of lock plates 1720 to kink, grip, or otherwise grasp tether 333 and prevents movement of tether 333 through the aperture. In some embodiments, epicardial anchor structures, 1700 and 1800, may move distally along tether 333 when lock plates 1720 are in the lock position and only proximal motion may be limited.

Optionally, reconfiguring locking plates 1720 between the lock and unlock position, or in other words pivoting the locking plates so as to grip or disengage tether 333, may be effected by axial rotation of a lumen body 1710 as shown in FIGS. 17B and 17C. Alternatively, a movable actuator or pin 1802, which engages locking plates 1720 in the unlock position, may be removed to allow the locking plates 1720 to assume the lock position. Rotation of lumen 1710 and/or removal of pin 1802 may be effected from along a working lumen to reconfigure locking plates 1720.

In operation, epicardial anchor 355 is positioned adjacent external wall EW of heart H and epicardial anchor structure, 1700 or 1800, is inserted over tether 333 in the variable force mode to adjacent epicardial anchor 355. A desired anchor force is then applied to epicardial anchor 355 and septal anchor 332 and epicardial anchor structure, 1700 or 1800, is reconfigured to the set force mode to lock epicardial anchor structure, 1700 or 1800, about tether 333 and prevent proximal movement of epicardial anchor structure, 1700 or 1800, relative to tether 333. The applied anchor force may inhibit migration of the anchors as described herein.

Returning now to FIG. 3L, epicardial anchor 355 may be slide or advanced along tether 333 until epicardial anchor 355 contact external wall EW (shown by position 351). As briefly mentioned above, FIG. 3M shows a force being applied by force application tool 314. Additional aspects of force application tool 314 are shown in FIG. 10. Force application tool 314 may be a relatively simple structure similar to a scale, typically having a force spring 313 and indicia 315 showing when a force in a desired range is being applied such as by showing deflection of the spring to a position within a desired range. By sliding the shaft 316 of the force application tool 314 over tether 333, engaging the surface of epicardial anchor 355 with a compression surface of the shaft 316, and applying force between the tether 333 and the force application tool 314 till the desired deflection is identified, the desired force may be applied between septal anchor 332 and epicardial anchor 355. While that force is applied, anchor set tool 359 may disengage the cam lock mechanism 363 of epicardial anchor 355, thereby reconfiguring epicardial anchor 355 from the variable-force mode to the set-force mode. Alternatively, if epicardial anchor structures, 1700 or 1800, are used, rotatable feature 1702 or movable actuator 1802 may be operated to reconfigure epicardial anchor structures, 1700 or 1800, to the set-force mode and thereby secure or anchor epicardial anchor 355 about tether 333.

The force application tool 314 and anchor set tool 359 can then be removed as shown in FIG. 3N and the tether 333 extending away from the heart from epicardial anchor 355 can be cut and removed, leaving epicardial anchor 355 and septal anchor 332 anchored or secured so that the septum SE and external wall EW contact or so a volume of the left ventricle LV is reduced. Pressure by epicardial anchor 355 against external wall EW inhibits blood flow out of the left ventricle LV along the epicardial access path, while pressure of septal anchor 332 against the septum SE inhibits blood flow from the left ventricle LV to the right ventricle RV. Known techniques can be used for closure of the vascular access of delivery catheter 326 and the minimally invasive access to the epicardium. FIG. 3O shows that the above process can be repeated so that multiple epicardial anchors 355 and septal anchors 332 are positioned against the septum SE and external wall EW to reduce a volume of the left ventricle LV.

Epicardial anchor 355 and/or septal anchor 332 may include an outer layer of ingrowth material, such as layer 362 of FIG. 10D, which promotes scar tissue growth around the anchors. The ingrowth material may comprise a polyester fabric. Similarly, an elongate flexible body 380 of ingrowth material may be positioned between the septum SE and external wall EW as shown in FIG. 3L to promote tissue growth between the septum SE and external wall EW after the septum SE and external wall are brought into engagement. The flexible body 380 may include an aperture that slidably receives tether 333 therethrough so that flexible body 380 extends laterally from tether 333. The aperture may rotationally couple flexible body 380 to tether 333 so as to facilitate orienting the flexible body 380 by rotation of tether 333. Flexible body 380 may be positionable between septum SE and external wall EW by advancement of flexible body 380 over tether 333.

Referring now to FIGS. 10, 10A, and 10D-10F, shown are the various tools that may be used in the process described in relation to FIGS. 3A-3O. FIGS. 10 and 10A show the delivery catheter 326, which includes a lumen 317 that extends between a proximal end 318 and a distal end 319. Various other catheters or tools, such dilating catheter 324, loading cartridge 334, and pusher tube 336 may be inserted partially or fully within lumen 317. Delivery Catheter 326 includes a hemostasis valve (not shown) located at the proximal end 318, which minimizes blood loss during the minimally invasive surgery.

FIGS. 10, 10A, and 10E show the dilating catheter 324 having the tapering threaded tip 325 and a lumen 323 extending between a proximal end 318a and a distal end 319a of dilating catheter 324. The guidewire 311 is insertable through the lumen 323 so that the dilating catheter may be inserted over the guidewire along an access path, which may be an arcuate path, and through one or more walls of the heart as described herein. FIGS. 10A and 10E show a detail view of the tapering threaded tip 325. The threads contact, grip, and/or cut tissue of the heart wall as the dilating cathter 324 is rotated and inserted through the wall. This minimizes the axial forces exerted against the heart wall, which may reduce arrhythmia and other conditions of the heart resulting from such axial stress. In some instances, the heart wall (e.g., septum SE and/or external wall EW) comprises tough scar tissue, which may be difficult to penetrate.

FIGS. 10 and 10F show aspects of the pusher tube 336 and loading cartridge 334. FIG. 10F shows the pusher tube 336 having 4 lumens, which include the guidewire lumen 339, through which guidewire 311 is inserted, and tether lumen 341, through which tether 333 is inserted. Guidewire 311 may be inserted within guidewire lumen 339 at a distal end 319b of pusher tube 336 and exit pusher tube 336 via guidewire port 343 at a proximal end 318b. Similarly, as shown in FIG. 10, tether 333 may be inserted within tether lumen 341 at distal end 319b and exit pusher tube 336 via tether port 345 at proximal end 318b. Loading cartridge 334 may be coupled with pusher tube 336 at distal end 319b and inserted within lumen 317 of delivery catheter 326.

FIGS. 10, 10D, and 10E show aspects of septal anchor 332, epicardial anchor 355, anchor set tool 359, and tether 333. Specifically, the figures show septal anchor 332 coupled with tether 333 at pivot point 333a. The figures also show epicardial anchor 355 with lumen 353 through which tether 333 is inserted as shown in FIG. 10E. FIG. 10D shows epicardial anchor 355 disconnected from anchor set tool 359. FIG. 10D also shows sheath 371, retractable post 367, and hooks 368 of anchor set tool 359 and shows outer layer 362, housing surface 366, lumen 353, and arms 364 of epicardial anchor 355. As described previously, hooks 368 are used to grip arms 364 and post 367 contacts housing surface 366 to actuate cam 363 upon actuation of rotatable cap 357 and thereby configure epicardial anchor 355 in either a variable force mode or a set force mode. As shown in FIG. 10E, epicardial anchor 355 is slidable along the length of tether 333 when epicardial anchor is in the variable force mode. When epicardial anchor is in the set force mode, epicardial anchor 355 may be slid toward septal anchor 332, but not away therefrom.

FIG. 10 also shows force application tool 314 having an elongate shaft 316, force spring 313, and indicia 315 as described previously. Indicia 315 may include a series of marks spaced along elongate shaft 316. Force spring 313 and indicia 315 are housed within main body 307, which may be made of a clear material so that indicia 315 is visible from outside main body 307. Force application tool 314 includes a lumen 309 that extends between a proximal end 318c and a distal end 319c through which tether 333 is inserted. Force application tool 314 applies a force against epicardial anchor 355 as tether 333 is tensioned from proximal end 318c and main body 307 is pushed toward epicardial anchor 355.

Referring now to FIGS. 10B and 10C, shown is another embodiment of a pusher tube 1036, which may be inserted through lumen 317 of delivery catheter 326. Similar to pusher tube 336, pusher tube 1036 includes four lumens. Guidewire lumen 1039 is a lumen through which guidewire 311 may be inserted. Guidewire lumen 1039 extends from distal end 1019 to guidewire port 1043 at proximal end 1018. Similarly, tether lumen 1041 is a lumen through which tether 333 may be inserted. Tether lumen 1041 extends from distal end 1019 to tether port 1045 at proximal end 1018. Pusher tube 1036 also includes a pair of opposed deployable arms 1031, which are housed within lumens 1052 and deployable axially and laterally therefrom. Deployable arms 1031 may be deployed so that the arms radially extend from pusher tube 1036. Deployable arms 1031 may then be engaged against an interior surface of one of the heart walls to stabilize pusher tube 1036 and/or delivery catheter 326 and facilitate in deployment of setpal anchor 332 and/or epicardial anchor 335. In some embodiments, pusher tube 1036 includes a malecot and/or balloon, which provides a similar function to deployable arms 1031. Further, in some embodiments, deployable arms comprise nitinol springs and are deployable from lumens 1052 or retractable within lumens 1052 upon rotation of main body 1050 or upon operation of an actuation device located at proximal end 1018.

Figure 11A:
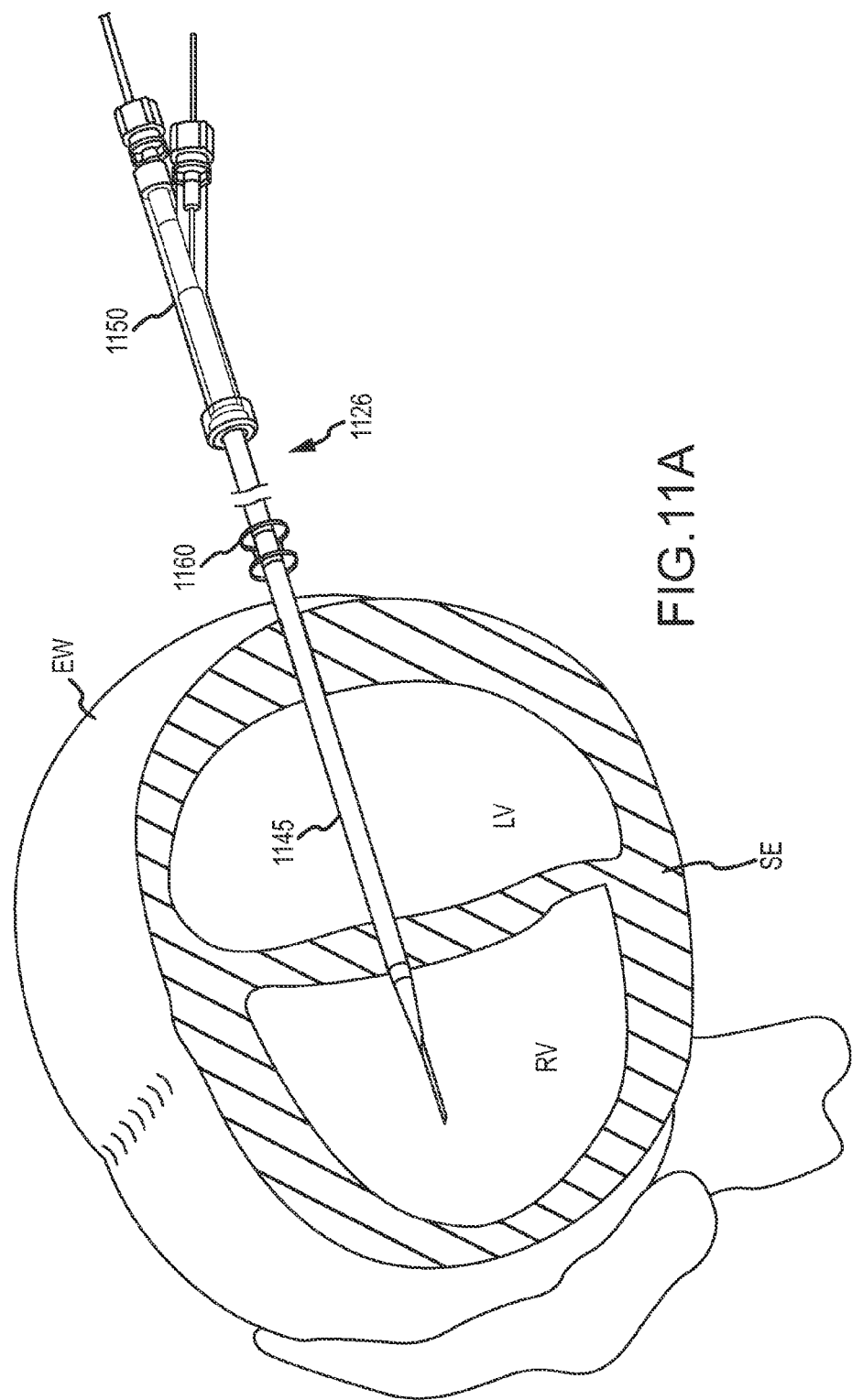
FIGS. 11A-11C illustrate an alternative over-the-wire dilating catheter, according to an embodiment of the invention.
Figure 11B:
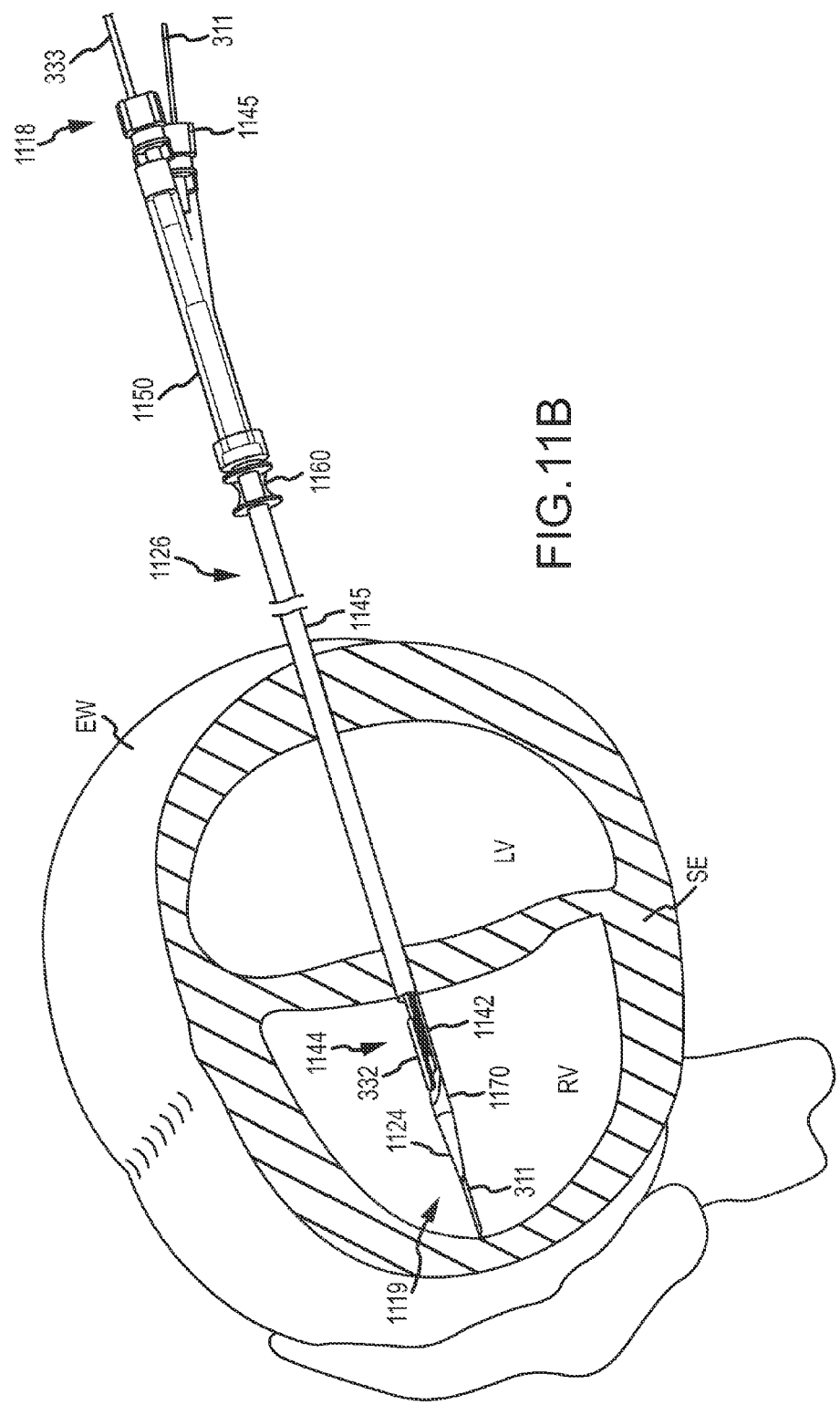
Figure 11C:
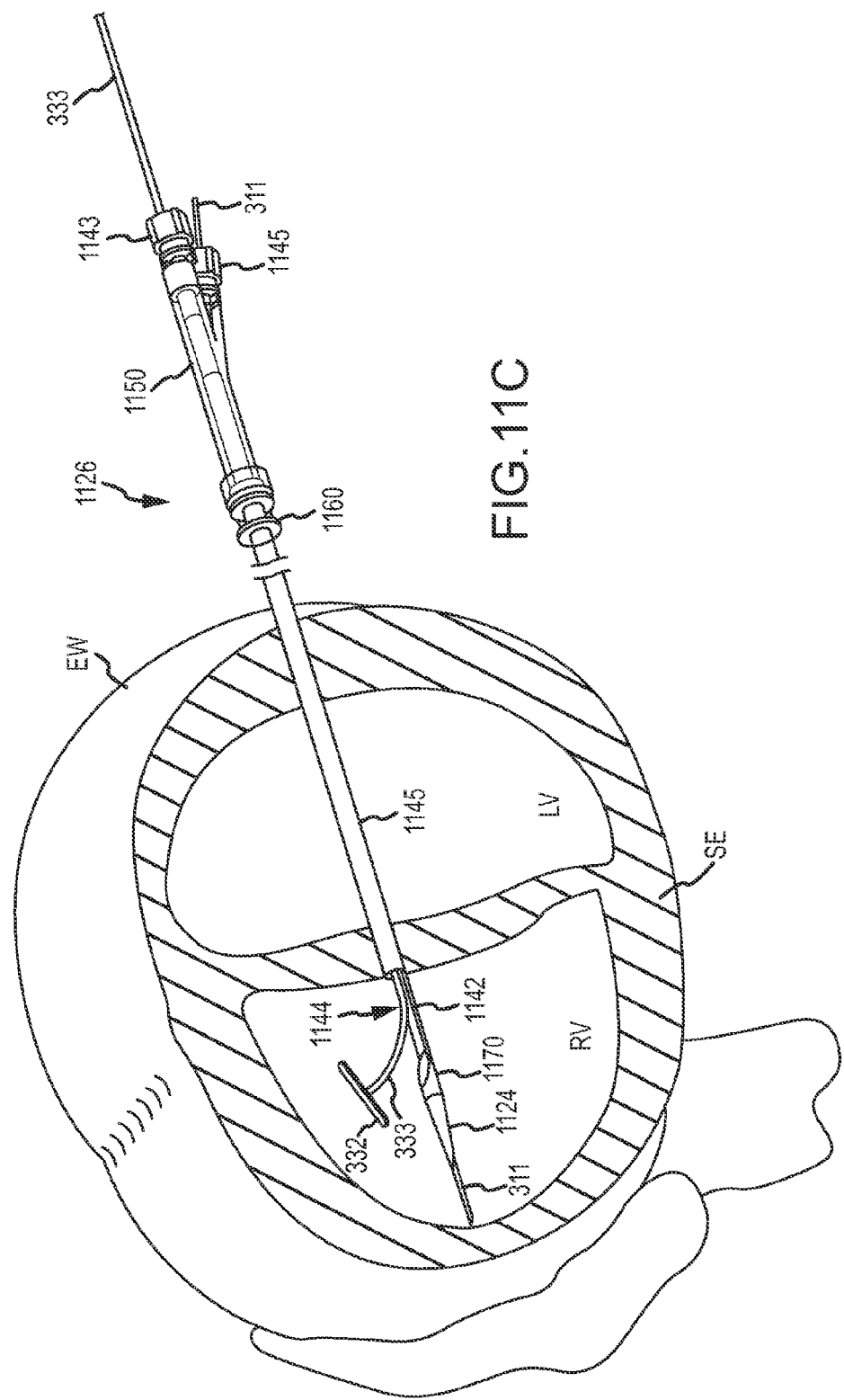

Referring now to FIGS. 11A-11C, shown is another embodiment of a delivery catheter 1126. Delivery catheter 1126 may replace the separate delivery catheter 326 and pusher tube 336 by combining these tools into one tool. Delivery catheter 1126 may include a catheter body 1142 having a tapered distal tip 1124 at distal end 1119 and a sheath 1145 disposed over catheter body 1142 proximally of tapered distal tip 1124. Sheath 1145 may be proximally retractable relative to catheter body 1142 to expose anchor receptable 1144, which houses septal anchor 332. Anchor receptacle 1144 may be coupled with tether port 1143 at proximal end 1118 so that tether 333 extends along the length of catheter body 1142 from proximal end 1118 to anchor receptacle 1144. Catheter body 1142 may include a guidewire lumen through which guidewire 311 may be inserted. The guidewire lumen may extend along catheter body 1142 and couple with guidewire port 1145 through which guidewire 311 exits delivery catheter 1126. Sheath 1145 may include a stop 1160 which limits proximal retraction of sheath 1145 by contacting main body 1150. In some embodiments, stop 1150 is positioned adjacent external wall EW and catheter body 1142 is advanced distally to expose anchor receptable 1144.

Septal anchor 332 may be laterally deployable from anchor receptacle 1144 as shown in FIG. 11C. Catheter body 1142 may include a sloped deployment member 1170 that facilitates in lateral deployment of septal anchor 332 from anchor receptacle 1144 as septal anchor 332 is distally advanced relative to delivery catheter 1126.

Operation of delivery catheter 1126 is similar to delivery catheter 326 described in FIGS. 3A-3O in that guidewire 311 is inserted through external wall EW and septum SE into right ventricle RV and delivery catheter 1126 is inserted over guidewire 311 into right ventricle RV. One difference is that septal anchor 332 need not include a lumen through which guidewire 311 is inserted since septal anchor 332 is housed within anchor receptable 1144 and inserted into right ventricle RV while housed within anchor receptable 1144. Tapered distal tip 1124 dilates the aperture through external wall EW and/or septum SE as delivery catheter is inserted through the respective wall. Although not shown, tapered distal tip 1124 may be threaded as described herein. After distal end 1119 of delivery catheter 1126 is positioned within right ventricle RV, sheath 1145 is proximally retracted (or catheter body is distally advanced) exposing anchor receptacle 1144. Septal anchor 332 is then laterally deployed from anchor receptacle 1144 via deployment member 1170 by distally advancing septal anchor 332 relative to catheter body 1142. With septal anchor 332 deployed within right ventricle RV, delivery catheter 1126 may be removed and epicardial anchor 355 secured to tether 333 as described herein to limit the volume of left ventricle LV. In some embodiments, delivery catheter 1126 may comprise a flexible material to allow delivery catheter 1126 to follow an arcuate epicardial access path defined by guidewire 311.

Figure 4A:
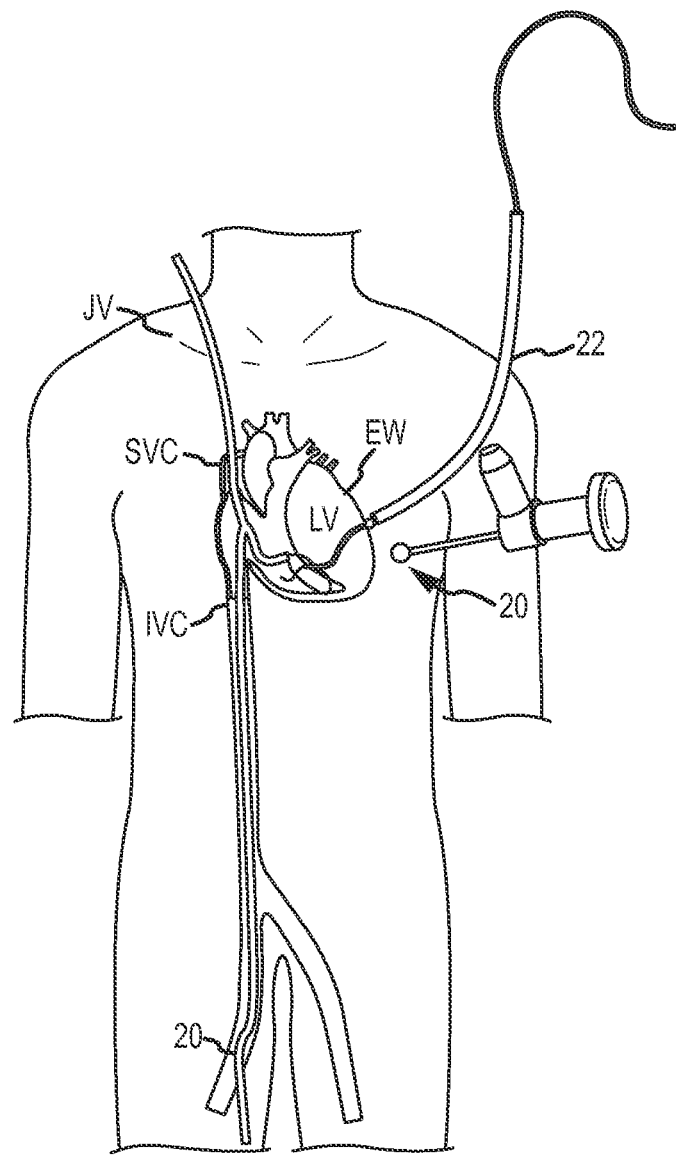
FIG. 4A schematically illustrates joining of a femoral access tool path through the right atrium and an endoscopic trans-epicardial access tool path by snaring a guidewire within the right ventricle of the heart, according to an embodiment of the invention.

Referring now to FIG. 4A, joining of an access path through the right atrium to an access path through the pericardium and epicardium by snaring of a guidewire within the right ventricle under thoracoscopic guidance 20 is schematically illustrated. The right atrial access path may extend into the arterial vasculature via the femoral artery FA and inferior vena cava IVC, via the jugular artery JA via the superior vena cava SVC, or the like. As can be understood with reference to FIG. 4B, a selected location for perforation of the external wall EW can be identified using an image from thoracoscope 20, optionally in combination with an image from another imaging modality (such as a prior or contemporaneous image from an ultrasound imaging system, an MRI imaging system, an X-ray or fluoroscopic imaging system, a CT imaging system, or the like). In exemplary embodiments, a rigid or semi-rigid shaft of an access tool 22 having a working lumen therethrough is advanced through the epicardium of the beating heart so that a distal end of the shaft is disposed within the left ventricle LV. Access tool 22 may comprise a relatively simple needle or trocar, and may have a proximal hemostasis valve at its proximal end so as to inhibit bloodflow through the lumen and facilitate insertion and/or removal of a guidewire and the like. In some embodiments, access tool 22 may have a tissue penetrating sharpened distal end to facilitate distal insertion, and/or a stylus may be removably disposed within the lumen. Optional embodiments of access tool 22 may have an energy delivery surface at or near the distal end so as to deliver radiofrequency energy, laser energy, or the like to facilitate penetrating the tissue of the external wall EW. Suitable RF penetrating structures may be commercially available from (or modified from those available from) Baylis Medical of Toronto Canada.

Figure 4B:
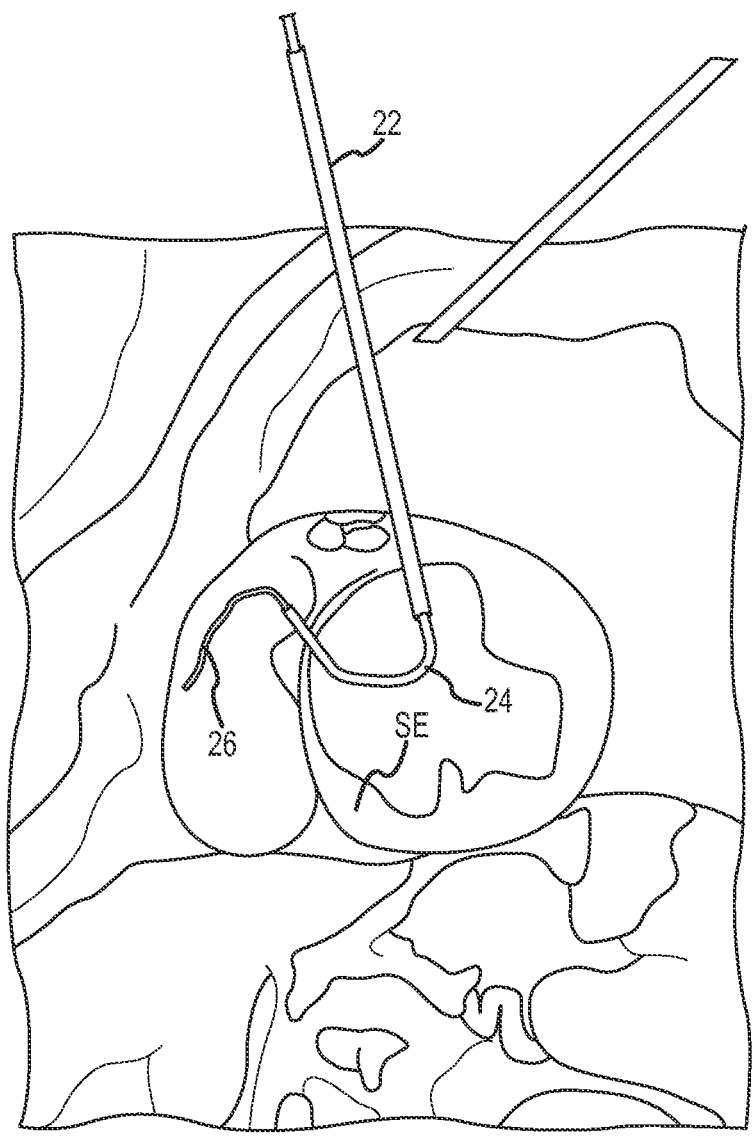
FIG. 4B schematically illustrates introducing a guidewire into a right ventricle of the heart through an external wall of the left ventricle and through the septum so as to form an epicardial access path, according to an embodiment of the invention.

Still referring to FIG. 4B, access tool 22 may optionally include a laterally deployable structure near the distal end so as to stabilize the access tool relative to the beating heart tissue around the left ventricle. Suitable deployable stabilizing structures may include a malecott, a pair of opposed deployable arms (optionally similar to those described below with reference to FIGS. 10B and 10C), or the like. The laterally deployable distal structure may be configured for engagement against an interior surface of the left ventricle LV or against the epicardial surface of the left ventricle (such as by having the deployable structure spaced proximally of the distal end). Regardless, once access tool 22 is disposed within the left ventricle, a catheter 24 may be advanced through the working lumen of access tool 22, into the left ventricle, and through a target location of the septum S. A guidewire 26 will also be inserted through the left ventricle and septum as shown. A variety of structures and techniques can be used for perforating the septum, with the catheter optionally being used to penetrate the septum in some embodiments, with the catheter optionally having a sharpened end, a removable stylus, an energy delivery surface, or the like. When catheter 24 perforates the septum, the catheter will often have steering capabilities so as to facilitate perforation at a target location, though in some embodiments catheter 24 may be steered using steering capabilities of the guidewire within the working lumen, a steering catheter extending around the catheter and through the working lumen of access tool 22, or the like. In other embodiments, guidewire 26 may be used to perforate through the septum, with the guidewire optionally having an energy delivery tip and/or steering capabilities with the catheter being advanced through the septum over the guidewire. Exemplary steerable guidewires with RF penetrating tips include those commercially available from (or may be derived from those available from) Baylis Medical of Toronto Canada.

A wide variety of alternative septum perforation approaches might be employed, including using atrial septum perforation structures and techniques (or structures and techniques derived therefrom). For example, mechanical systems may employ a sharpened distal tip and axial penetration (such as using structures commercially available from—or structures derived from the SafeSept transseptal guidewire commercially available from Adaptive Surgical, LLC; the Across Transseptal Access System commercially available from StJude, or the like, a rotatable angled blade, the transseptal puncturing structures and methods described by Wittkampf et al, in US2011/0087261, or the like. RF systems may employ a proprietary tissue penetrating structure or may energize an off-the-shelf transseptal needle with RF energy, as was described by Knecth et al. in an article entitled "Radiofrequency Puncture of the Fossa Ovalis for Resistant Transseptal Access," Circ Arrhythm Electrophysiol 1, 169 (2008). Laser-energy transseptal approaches may also be employed, including structures commercially available from (or derived from those commercially available from) Spectranetics and others.

Once catheter 24 is advanced through the septum, the working lumen of the catheter may be used to access the right ventricle from outside the patient, with the guidewire optionally being removed and replaced (particularly when the guidewire has been used to perforate the septum) with another guidewire, or remaining for use in joining the access paths. To facilitate use of catheter 24 as a right ventricle access tool and swapping guidewires or the like, a hemostasis valve may be provided at a proximal end of the catheter.

Figure 4E:
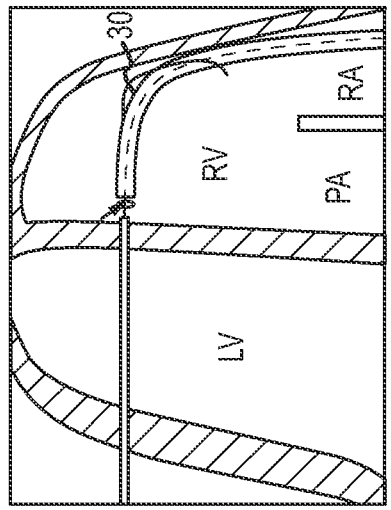
FIGS. 4C-4E schematically illustrate joining a right atrial access tool shaft with an endoscopic trans-epicardial access tool shaft within the right ventricle by coupling a guidewire and snare advanced along the shafts and into the right ventricle, according to an embodiment of the invention.
Figure 4C:
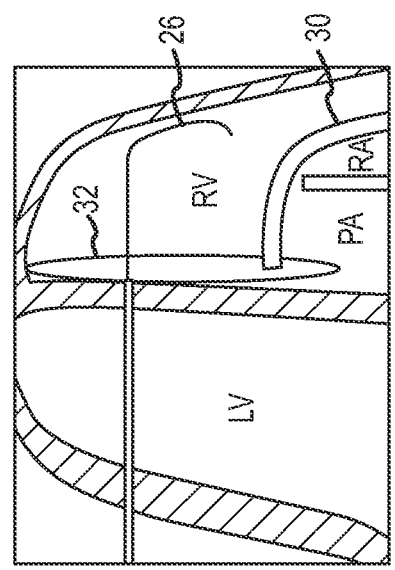
Figure 4D:
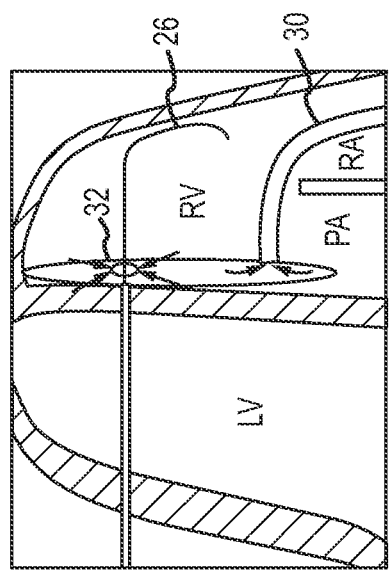

Referring now to FIGS. 4C-4E, a distal end of catheter 30 may be advanced to the right ventricle RV through the right atrium RA and associated vasculature using known techniques, so that catheter 30 provides a right ventricle access tool. Optionally, a snare tool has a distal portion configured to engage a distal portion of the guidewire. For example, distal snare 32 may be separated from a proximal end of a snare body by sufficient length of the snare body to allow the snare to be manipulated within the right ventricle from the proximal end of catheter 30. Snare 32 may be biased to open when advanced beyond catheter 30, allowing the catheter to be positioned near the septum around the epicardial path of catheter 24. Advancing guidewire 26 through the opening of snare 32 and withdrawing snare 32 into catheter 30 so that the guidewire is bent as it enters the distal end of catheter 30 axially couples the guidewire to the snare.

Figure 5A:
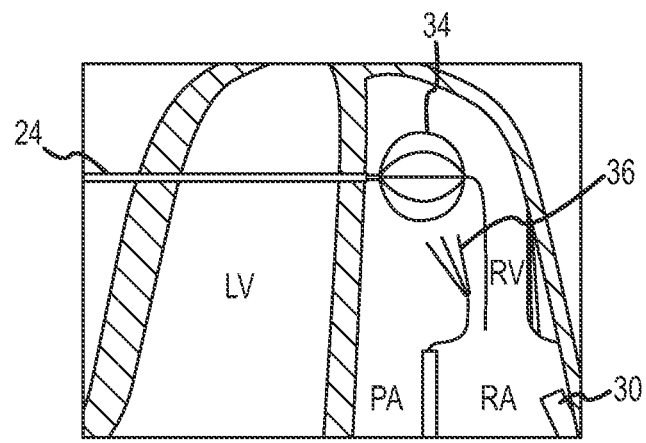
FIGS. 5A and 5B schematically illustrate alternative techniques for joining a right atrial access tool shaft and an endoscopic epicardial access tool by snaring a guidewire within the right ventricle or right atrium of the heart using a basket snare, according to an embodiment of the invention.
Figure 5B:
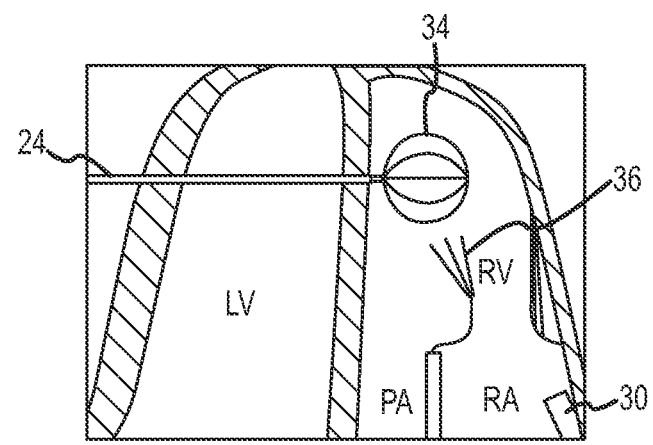
Figure 6:
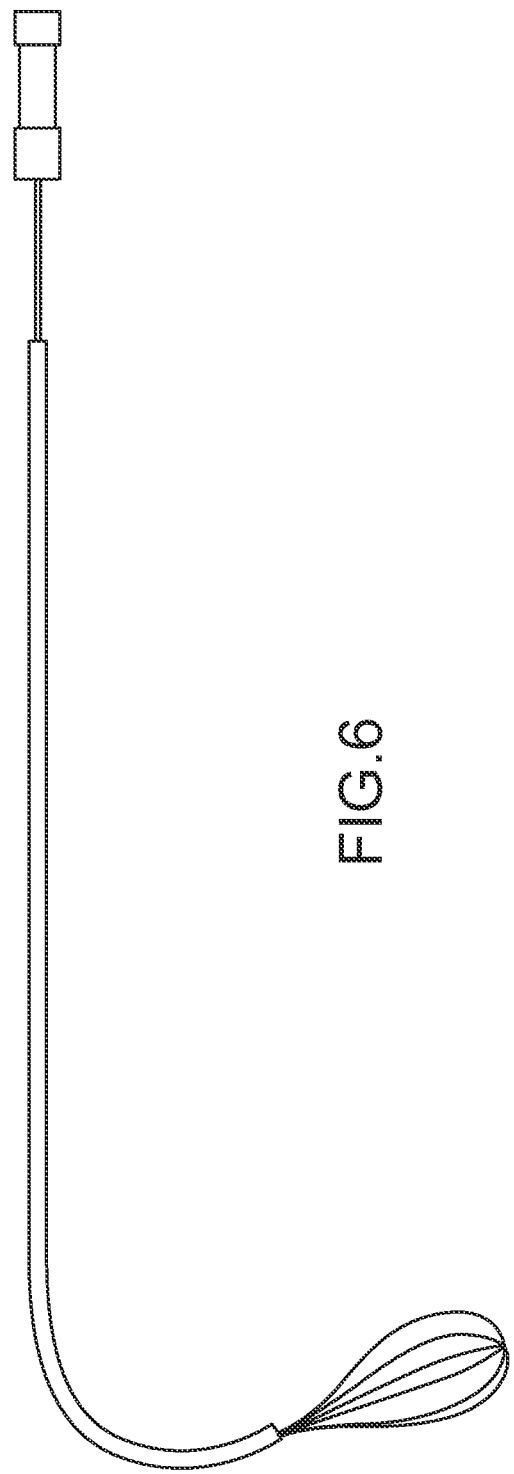
FIG. 6 illustrates a basket snare and associated access catheter configured for use in the right ventricle, according to an embodiment of the invention.

Referring now to FIGS. 5A and 5B, there may be advantages to employing alternative elongate flexible bodies to couple the access paths within the heart. For example, a guidewire-like elongate body with a proximal end and a distal portion formed as a basket 34 may be expanded in the right ventricle so that the basket encompasses a volume within the right ventricle. In some embodiments, the basket may be withdrawn back into catheter 24 or 30 so as to capture a guidewire extending from the other, thereby joining the paths. In other embodiments, a guidewire-like elongate flexible body 36 having short lateral distal protrusion or barb can be advanced a relatively short distance into a target portion of the basket and withdrawn back into the catheter so as to capture a member of basket 34, with the target portion of the basket being separated from sensitive heart tissues (such as valve leaflets or chordae) by the expansion of the basket. Optionally, the basket 34 may be advanced toward or into the right atrium before engaging the basket with the distal portion of flexible body 36. An exemplary basket structure and associated access catheter are shown in FIG. 6.

Figure 7:
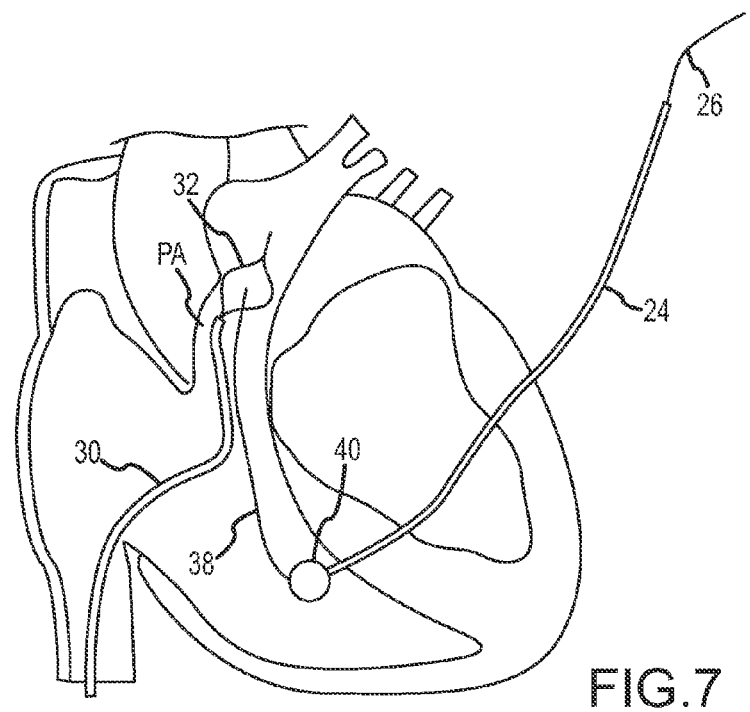
FIG. 7 schematically illustrates joining a right-atrial access tool path with a trans-epicardial access tool using a snare and associated guidewire configured for coupling within the pulmonary artery, according to an embodiment of the invention.
Figure 8:
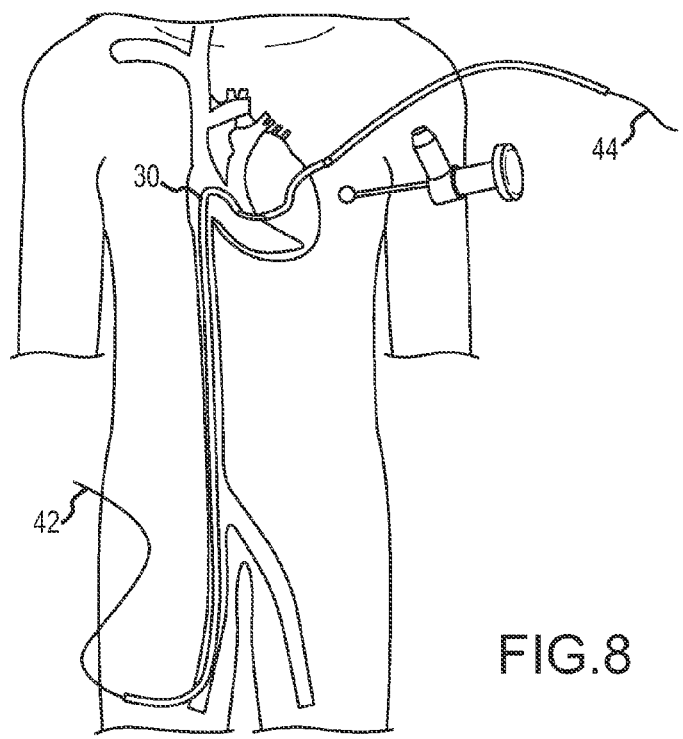
FIG. 8 schematically illustrates a guidewire that has been pulled along paths joined within the right ventricle so as to extend from outside the patient, through the right atrium, through the right ventricle, through the septum, through the left ventricle, through an exterior wall of the heart, and back outside the patient, according to an embodiment of the invention.

Referring now to FIG. 7, still alternative distal end portions may be used to help couple the flexible bodies advanced into the heart via the right atrial and epicardial access paths. In this embodiment, catheter 30 is advanced through the right atrium and the right ventricle to the pulmonary artery PA. Snare 32 is expanded in the pulmonary artery PA. A distal balloon 40 mounted to a flexible tubular body 38 is advanced through catheter 24 into the right ventricle. Balloon 40 is inflated from a distal end of the flexible body 38 via an inflation lumen of the flexible body, and the balloon is allowed to flow with the blood of the heart into a pulmonary artery PA. The balloon is captured by the snare. Note that the access catheter 24, 30 associated with the various flexible bodies described above may be switched, so that (for example) balloon 40 may be advanced through catheter 30 along the right atrial access path, while snare 32 may be advanced along catheter 24 along the epicardial approach. Regardless of the specific end portions of the flexible bodies employed to axially couple the flexible bodies, coupling of the pathways allows guidewire 26 to be inserted into the body along one of the paths and withdrawn out of the body from along the other path so that both a first end 42 and a second end 44 of the guidewire are disposed outside the heart and the patient. The result is the guidewire extending from a first end disposed outside the patient, into the right ventricle of the heart along the epicardial access path, and back out of the heart and the patient through the left ventricle along the epicardial access path, as shown in FIG. 8.

Figure 9:
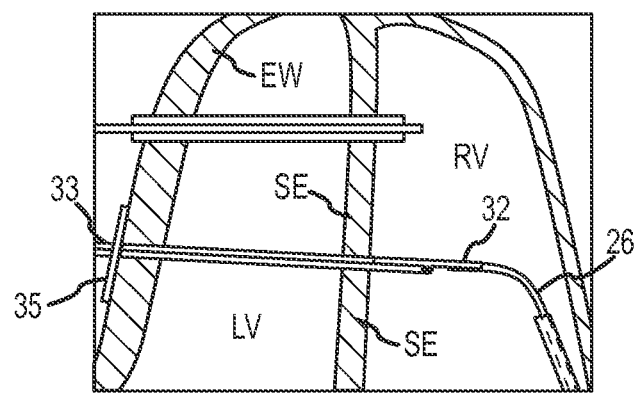
FIG. 9 schematically illustrates expansion of a path through the left ventricle over a guidewire, delivery of an anchor and adjacent tension member through the expanded path and over the guidewire, and controlling movement and orientation of the anchor within the right ventricle using a guidewire extending along a joined path, according to an embodiment of the invention.

Referring now to FIG. 9, once guidewire 26 extends from the first end, into the right ventricle along the epicardial access path, and back out the heart and patient through the left ventricle along the epicardial access path, septal anchor 32 and tether 33 may be advanced over guidewire 26 into right ventricle RV and/or adjacent septum SE. Tether 33 may be advanced over guidewire 26 as shown in FIGS. 13A-14C and may be advanced ahead of septal anchor 32 so that tether 33 extends from adjacent septum SE, through left ventricle LV, to outside the patient body as shown in FIG. 9. Guidewire 26 may then be removed so that septal anchor 32 may rotate relative to tether 33 as described herein. Epicardial anchor 35 may them be coupled with tether 33 and advanced adjacent external wall EW, a force may be applied between epicardial anchor 35 and tether 33, and epicardial anchor 35 may be secured relative to tether 33 and septal anchor 32 as described herein.

Referring now to FIGS. 13A-14C, alternative embodiments of the systems may be configured to deliver septal anchor 32 to the right atrium along the right atrial path, typically with septal anchor 32 trailing behind tether 33. An end of tether 16 is generally disposed opposite of anchor 32, and may include features to maintain the tether in alignment along the guidewire, and may also axially couple the tether to the guidewire. For example, a channel such as angled channel, 64a or 64b, may receive the guidewire 31 therein, allowing the tether to be pushed axially over the guidewire. One or more additional channels 66 (shown in FIG. 13C) through tether 33 toward anchor 32 may help limit bowing of the tether 33 away from guidewire 31 when tether 33 is pushed axially over guidewire 31. As can be understood with reference to FIGS. 14A-14C, end 70 of tether 33 is advanced over guidewire 31 and into a proximal hemostasis valve 29 of catheter 30. By continuing to push tether 33 into catheter 30, and/or by pulling guidewire 31 from the end extending from the epicardial path, end 70 of tether 33 may be advanced into and through the septum SE and external wall EW so that end 70 is disposed outside the heart and the patient. Optionally, tether 33 may be advanced along the epicardial path alongside guidewire 31. In other embodiments, catheter 30 or another catheter body may be advanced over the guidewire with tether 33 disposed in a lumen.

Referring now to FIGS. 16A-16D, an epicardial access tool may facilitate both access to the epicardium and hemostasis of the epicardial access path. A shaft of the epicardial access tool extends from a proximal handle to a circumferential series of distal radial compression features. A working lumen of the access tool shaft allows the various access tools to be advanced along a tissue tract from outside the patient to an epicardial surface region encompassing the epicardial access path. The compression features are oriented to engage tissue of the external wall and urge the engaged tissue radially inwardly when the handle is actuated. In the exemplary embodiment, filaments extend axially from the handle along the shaft to each compression feature, and then turn laterally from that compression feature to another compression feature. Actuation of the handle pulls the filaments, thereby pulling the compression features radially inwardly.

Alternative epicardial access tools may employ suction to grip and stabilize the epicardial surface of the heart, somewhat analogous to the engagement between known heart stabilization tools and the heart as used for beating-heart coronary arterial bypass grafting and the like.

Referring now to FIGS. 19A-19D, a variety of minimally alternative anchor locking structures and access methods may be employed to decrease collateral tissue trauma when applying the controlled anchoring force. Such minimally invasive anchor locks may benefit from a tissue-engagement component that distributes anchoring loads laterally between anchors so as to promote apposition of the walls of the heart along a desired contour and help provide the desired ventricular shape after implantation of a multi-anchor implant system. Toward that end, a folding anchor component 1911 may comprise an at least substantially rigid elongate body having a passage traversing therethrough, with a channel extending along opposing surfaces of the body from the aperture. One of the channels may optionally extend through the body, allowing the body to be advanced laterally over tether 1916 so that the tether extends through the body at the passage. Other embodiments may employ passages in the form of apertures, so that the tether 1916 is passed axially through the passage. Regardless, the channels receive the tether 1916 so that the anchor component 1911 can pivot toward axial alignment with tether 1916, allowing the anchor component to be advanced over tether 1916 through a working lumen of an access tool or sheath 1913, as shown in FIG. 19B. Once anchor component 1911 is distal of sheath 1913 and proximal of the epicardial surface of the heart H, the anchor component 1911 can be pivoted relative to tether 1916 and slid distally along tether 1916 into engagement with the epicardial surface of heart H, as shown in FIGS. 19C and 19D. A relatively small profile (as compared to the pivoted anchor component 1911) locking anchor component, such as epicardial anchor 355, can then be advanced axially over tether 1916 through sheath 1913 and into engagement with the anchor component 1911 so as to provide the desired anchoring force. Anchor component 1911 may comprise a metal or high-strength polymer structure, such as a stainless steel, a Nitinol shape memory alloy, PEEK, or the like.

While the exemplary embodiments have been described in some detail for clarity of understanding and by way of example, a variety of modification, adaptations, and changes will be obvious to those of skill in the art. Hence, the scope of the present invention is limited solely by the appended claims.

EXPERIMENTAL

Experimental Setup

One of the purposes of the experiment was to obtain information on the tolerance of the scar tissue of the heart to pressure applied by anchors placed to accomplish the heart reconstruction described in the instant application. Stated differently, one purpose of the experiment was to apply differing increments of compressive force on the apposed walls to identify the histologic failure threshold of increasing the compressive force on anchors in the performance of the heart reconstruction procedures described herein. Early experience with procedures demonstrated that when applied compression forces were not rigidly controlled, instances of erosion and/or migration were observed within 5-6 weeks of the procedure. In some studies, one anchor pair was smaller in width (though equal in length) than the other, and the amount of compression applied to the anchors after the walls came into contact was unknown.

Some studies have demonstrated an asymmetry of force fields when the anchors are of disparate sizes. In the instant experiment, the erosion was corrected in two ways:

1. Anchors were made identical in size. The hinged (internal) anchor was increased by approximately 60% in width, bringing it into equality with the locking (external) anchor. This change effectively distributed the forces over a greater amount of tissue, and made force fields symmetric. The delivery system was modified to accommodate this change in size.

2. A means of strictly measuring the compression force was used. The compression force general refers to the force applied by the anchors on the tissue after walls come into contact. A force application tool, such as the tool described in the instant application (i.e., 314) was used and allowed a measured force to be applied as anchors and walls were apposed. The force application tool also allowed for the measurement of the force applied on the anchors by systolic function of the heart.

The total force on any anchor pair was assumed to be the sum of (1) tension resulting from contractile power of the ventricle, and (2) additional compression applied after walls reach actual contact. In the experiment, two anchors of approximately equal size were used to exclude a portion of left ventricle (LV) scar. Specimens were free of either erosion or migration at 3 and 5 weeks post deployment. Further, the walls demonstrated roughly 100% fusion with no untoward anatomical changes.

Experiment Model

An ovine model was used as it provides similar anatomy regarding size and cardiovascular structure and simulates adult human clinical application. The chronic ovine model, in contrast to the porcine, also does not exhibit cumbersome body growth changes over time. In addition, ovine blood provides a rigorous hematological challenge for biocompatibility evaluation. As such, the described procedure was performed on sheep weighing 55 kg±5 kg.

The study addressed infarction of the homonymous or left anterior descending artery (LAD) and its branches. The model for these purposes was surgical ligation or trans-coronary occlusion of the homonymous artery at a point 40% of the distance from the apex of the heart followed by ligation of diagonal branches at the same level. After occlusion a delay period between 8 or more weeks was used for the development and maturation of the scarred tissue.

Procedure Groups

Each animal was subjected to the following procedure: 1) Coronary occlusion to induce ischemic cardiomyopathy. 2) Delay of 8 weeks for development of scar and left ventricle aneurysm. 3) Baseline echo, followed by randomization into four groups of 2 sheep each. 4) ECVR procedure with variation in apposition pressures as follows: a) group 1—Ventricular Contractile Force (VCF)+2N (i.e., 2 Newtons); b) group 2—VCF+4N; c) group 3—VCF+6N; and d) group 4—VCF+8 N. 5) Delay of 5 weeks until sacrifice. 6) Explant of device and gross examination. 7) Histopathology of myocardium.

EVCR Procedure Description

An ECVR was performed through the following steps:

1) Access is obtained to the left ventricle through an anterior left thoracotomy, sometimes including the removal of the $6^{th}$ rib for easier access.

2) Sites for anchor placement are selected and the animal is heparinized.

3) A large gauge, custom shaped needle is advanced through the scarred portion of the anterior wall of the left ventricle, using echo guidance, to the inter-ventricular septum, and using pressure guidance, through the inter-ventricular septum and into the right ventricle.

4) A guidewire is advanced through the needle and out the RV outflow tract using fluoroscopic guidance.

5) The needle is removed and a catheter/dilator/anchor ensemble is advanced over the guidewire and into the RVOT.

6) The sheath is retracted, exposing the anchor. The anchor rotated to the proper orientation, and is retracted against the septum as the sheath is removed.

7) A secondary, locking anchor is delivered over the tether and against the epicardium.

8) The process is repeated two to four times depending on the extension of the scar.

9) After all sets of anchors are in place they are sequentially cinched. This step was accomplished by: i) Using the Pressure Gauge device in the "locked" position, and the Locking Anchor cam in the "unlocked" position, the Locking Anchor is advanced while the Tether is pulled for counter-traction. It is advanced until tactile resistance confirms the walls are in contact. The Tether is marked where it exits the core of the Pressure Gauge. ii) The Pressure Gauge is then withdrawn such that walls are no longer in contact, but engaged adequately by both anchors, such that the contractile forces on the anchors can be measured by the Pressure Gauge. iii) The Pressure Gauge is then advanced as the Tether is retracted, until the measured contractile force is exceeded by 2N. iv) With the Tether held in rigid position relative to the Pressure Gauge, the lock on the cam of the Locking Anchor is set to "locked" position, and then removed. v) The Tether is checked to ascertain that the mark set in step "i" above is at the site where the Tether exits the Pressure Gauge, establishing that the walls are in apposition. vi) These steps are repeated for each individual anchor pair.

10) Once all sets are locked in place the tethers are cut with an appropriate cutting catheter.

Experimental Results

Fully mature *Ovis aries* (sheep) were used in the study as the sheep have hearts that are similar in size and structure to humans. The sheep hearts also lack the extensive collateral coronary circulation of other large animals, making the infarction model more reliable and the size of infarction more consistent. Further, unlike swine, since the sheep are mature, the subject animals will not grow during the prolonged observation period.

Pre- and Post-Myocardial Infarction Procedure

Five sheep were acclimated to the test facility 1 week before the initiation of the study. Each sheep received daily beta-blockers orally (approx.: atenolol 25 mg), beginning 2 days prior to the myocardial infarction (MI) and continued for 3 days after Ml creation. Animals were fasted (solid food) for 24-28 hours prior to anesthesia. Animals were anesthetized following standard protocol. The animals were then transferred to a cath lab, placed on the table with a water-circulation-heating pad, and attached to the anesthesia and ventilator unit. General anesthesia was maintained. For the duration of the study, monitoring was performed continuously of the animal's vital signs (heart rate, respiration rate, 02 pulse oxymeter, blood pressure, and the like), and recorded at approximately 15-minute intervals. Under general anesthesia, all animals were induced with myocardial infarction using coronary artery coil emobilization. Via the femoral artery, the left coronary artery was cannulated with a guiding catheter under fluoroscopic guidance and baseline coronary angiography was performed. A coronary guidewire and a coronary infusion catheter were then advanced into the middle Left Anterior Descending (LAD) coronary artery. Then the coronary guidewire was removed and the proper size of coronary coil was delivered into the LAD to block the coronary blood flow after the first diagonals of the LAD to induce myocardial infarction. Coronary angiography was performed to verify total occlusion and sentinel angiograms were taken every 15-20 minutes to ensure complete and persistent occlusion. Continuous ECG and hemodynamic monitoring assessed the evolving infarction for 120 minutes after coronary artery embolization. Amiodarone was used with a loading dose of 150 mg IV prior to ischemia, followed by an IV drip (25 mg/hour) maintained for 1-6 hours following induction of anesthesia.

Following angiography, the catheters and sheath were removed. Hemostasis was obtained by manual pressure. Post procedure, Buprenorphine (0.01-0.02 mg/kg IM) was administered for routine pain management. The animals were also given Cefazolin (1 g IV) to prevent infections and Lidocaine (1 OOmg IM) to prevent arrhythmia. Post-operative recovery and care of animals followed SCCR's standard procedure.

Anchor System Deployment Using Epicardial Catheter-Based Ventricular Reconstruction Procedure 130±11 Days post Ml, animals were anesthetized using standard protocol. The heart was exposed by means of a left thoracotomy through the fifth intercostal space. The pericardium was opened and retracted with stay sutures. Intravenous heparin was administered to maintain an activated clotting time of approximately 250 seconds. The ECVR procedure was performed using the following steps: 1) A needle was advanced through the scarred portion of the anterior wall of the left ventricle, using echo guidance, to the interventricular septum, and using pressure guidance, through the interventricular septum and into the right ventricle (RV). 2) A guidewire was advanced through the needle and out the RV outflow tract using fluoroscopic guidance. 3) The needle was removed leaving the guidewire within the PA. 4) A screw tip dilator was advanced by rotating first through the anterior wall of the left ventricle and then through the interventricular septum. 5) The dilator was then removed and a second dilator with the introducer was positioned over the guidewire and into the Right Ventricular Outflow Tract (RVOT). 6) The second dilator was the removed leaving the guidewire within the PA and the tip of the introducer 2 cm across the septum. 7) The internal anchor assembly was then passed over the wire and out the introducer. 8) The guidewire was then removed allowing the anchor to be rotated and retracted against the septum. 9) The introducer was then removed leaving the anchor and tether in position. 10) An external anchor (e.g., a locking anchor) was then placed over the cut tether and against the epicardium. 11) Multiple anchor pairs were placed in each animal.

Four animals had a total of two anchor pairs whereas one animal had a total of three anchor pairs depending on the extension of the scar. After all sets of anchors were in place they were sequentially cinched starting from the highest pair. A force gauge as described in the instant application was used to evaluate the compression force applied over and above that measured attributable to ventricular contractile forces by 2, 4, or 6 Newtons as shown in Table 1 below.

TABLE 1

| Number of Animals | Compression Force |
| --- | --- |
| 1 | Ventricular Force + 2N |
| 2 | Ventricular Force + 4N |
| 2 | Ventricular Force + 6N |

Once all anchor sets were locked in place the tethers were cut leaving 2-3 mm outside the external anchor. Post-procedure recovery and care of the animals followed standard operating procedures.

Results

The deployment of the anchors via the ECVR procedure was successful in this study. There were no unanticipated events observed in the study. Apposition of the walls was evident immediately post implant and maintained at six weeks post implant. As shown in Table 2 below, end systolic volume, end diastolic volume, stroke volume, and ejection fraction were measured at several timepoints: (1) prior to the creation of myocardial infarction (baseline), (2) 6-8 weeks post myocardial infarction, (3) immediately after the implantation of the anchor system, and (4) 6 weeks after the implantation of the anchor system.

TABLE 2

|  | Baseline* (Mean) | Pre-Implant** (Mean) | Immediately Post-Implant (Mean) | 6 Weeks Post-Implant (Mean) |
| --- | --- | --- | --- | --- |
| End Systolic Volume | 19.70 | 39.79 | 25.72 | 25.68 |
| End Diastolic Volume | 44.50 | 63.02 | 51.69 | 48.29 |
| Stroke Volume | 24.80 | 23.23 | 25.96 | 22.61 |
| Ejection Fraction (%) | 56 | 37 | 50 | 47 |

*Prior to myocardial infarction
**6-8 weeks after myocardial infarction and before the implantation of the anchors All coronary artery coil embolization-induced myocardial infarcts led to diminished ejection fractions (EF) and increased LV volumes. Six (6) weeks post implantation of the anchors resulted in significant reduction in End-Systolic and End-Diastolic Volumes (ESV, EDV). A significant increase in Ejection Fraction (EF) was observed. The Stroke Volume (SV) remains unchanged as expected. Table 3 below summarizes the changes in LV volume post-infarct/pre-implant and six (6) weeks after implant.

TABLE 3

|  | Pre-Implant** (Mean) | 6 Weeks Post-Implant (Mean) | P-Value |
| --- | --- | --- | --- |
| End Systolic Volume | 39.79 | 25.68 | 0.0004 |
| End Diastolic Volume | 63.02 | 48.29 | 0.01 |
| Stroke Volume | 23.23 | 22.61 | 0.84** |
| Ejection Fraction (%) | 37% | 47% | 0.03 |

*6-8 weeks post coronary artery coil embolization-induced myocardial infarction
**Stroke volume remains roughly unchanged as anticipated Conclusion The anchors were successfully deployed utilizing the ECVR procedure in a myocardial-infracted heart. A significant reduction in ESV and EDV, and an increase in EF were evident in the study. Histologic examination of lung, brain, liver, and kidney on all animals demonstrated no evidence of embolic events. Implantation of anchors in an infarct model in sheep and retrieved at six (6) weeks post implant showed good tolerance of the device characterized by minimal foreign body response, fibrous tissue formation around the device and no adverse subjacent endocardial changes and no adverse levels of necrosis or structural compromise of the pre-existing infract scar. The structural integrity of the ventricular infarct scar was preserved at the site of implantation. The device produced marked reduction of the dilated ventricular lumen at the level of the infarct in all explants. Complete endothelial coverage of internal anchors was observed in all cases. No pressure necrosis was observed in any animal, regardless of whether the walls were apposed with a tissue-compression force, (force applied over and above that measured attributable to ventricular contractile forces) of 2, 4, or 6 Newtons. All five (5) of the subject animals improved, with changes on measured volumes as noted in the table above.

What is claimed is:

1. A method for inhibiting migration of anchors of a heart implant device adjacent walls of a heart within a patient body, the method comprising:
   positioning a first anchor in engagement with a first wall of the heart, the first anchor being coupled with a tension member;
   positioning a second anchor in engagement with a second wall of the heart, the second anchor being slidably coupled with the tension member so that the second anchor may slide proximally and distally along a length of the tension member;
   applying an anchor force between the tension member and the second anchor by engaging the second anchor with a tension device, the anchor force being applied so that the first anchor provides a force urging the first wall toward the second wall and the second anchor provides a force urging the second wall toward the first wall, wherein the tension device comprises a shaft extending from a proximal end to a distal end, a lumen through which the tension member is inserted, and a tube that is slidably disposed over the shaft, the tube including a compression spring and indicia that provide an indication of the anchor force applied being within a desired range, and wherein the anchor force is applied by tensioning a portion of the tension member extending proximally of the tension device; and securing the second anchor relative to the tension member while the anchor force is applied so as to restrict proximal movement of the second anchor along the tension member and maintain the anchor force.

2. The method of claim 1, wherein the second anchor comprises a variable force mode that allows the second anchor to slide proximally and distally along the tension member, and wherein the second anchor further comprises a set force mode that inhibits movement of the second anchor proximally along the tension member.

3. The method of claim 2, wherein the second anchor is reconfigured from outside the patient body.

4. The method of claim 2, wherein the second anchor comprises a lumen through which the tension member is inserted and a lock, and wherein the method further comprises operating the lock to reconfigure the second anchor from the variable force mode to the set force mode, or vice versa.

5. The method of claim 4, wherein the lock comprises a spring and a cam disposed adjacent the lumen or wherein the lock comprises a spring and lock plate disposed adjacent the lumen, and wherein operating the lock comprises biasing the lock plate or the cam against the tension member in the lumen.

6. The method of claim 4, wherein the lock is operated from outside the patient body.

7. The method of claim 1, wherein the first anchor is inserted distally of the first wall over a guidewire.

8. The method of claim 7, wherein the first anchor is inserted in a low profile configuration, and wherein the first anchor is deployable laterally relative to the tension member to a deployed configuration.

9. The method of claim 1, wherein the anchor force is sufficient to bring the first wall into engagement with the second wall, and is insufficient to induce passage of the first anchor through the first wall.

10. The method of claim 9, further comprising advancing an intermediate body of an ingrowth material along the tension member so that the intermediate body of ingrowth material is disposed between the first wall and the second wall before the walls are brought into engagement, extending the intermediate body of ingrowth material laterally from the tension member, and rotationally orienting the intermediate body of ingrowth material by rotating the tension member, the ingrowth material promoting tissue growth between the first and second wall.

11. The method of claim 1, wherein the anchor force comprises a force of between about 2N and about 6N.

12. The method of claim 1, wherein the anchor force comprises a force of between about 3N and about 4N.

13. The method of claim 12, wherein the tension device is configured such that the anchor force cannot exceed 4N.

14. The method of claim 1, wherein applying the anchor force comprises:

engaging the second anchor with the tension device in a first mode of operation to urge the first wall toward the second wall;

normalizing a force indicator of the tension device; and applying a force to the second anchor with the tension device in a second mode of operation, wherein the tension device in the second mode of operation indicates the force applied to the second anchor.

15. The method of claim 1, wherein the first anchor and the second anchor are substantially the same size.

16. A method for inhibiting migration of anchors positioned adjacent walls of a chamber of a heart, the method comprising:

inserting a first anchor distally of a first wall of the heart, the first anchor being pivotally coupled with a tension member that extends from the first anchor, across the chamber of the heart, to proximally of a second wall of the heart;

positioning a second anchor proximally of the second wall, the second anchor being slidably coupled with the tension member in a variable force mode so that the second anchor slides proximally and distally along the tension member;

advancing the second anchor distally along the tension member via a tension device disposed outside the heart;

urging the first wall toward the second wall by engaging the second anchor with the tension device while the tension device is in a locked configuration;

normalizing a force indicator of the tension device;

adjusting the tension device to an unlocked configuration;

applying an anchor force to the second anchor with the tension device in the unlocked configuration, wherein the anchor force inhibits migration of the first and second anchors relative to the first wall and the second wall and wherein the tension device in the unlocked configuration indicates the anchor force via the force indicator; and reconfiguring the second anchor from the variable force mode to a set force mode, the set force mode securing the second anchor relative to the tension member by inhibiting proximal movement of the second anchor along the tension member.

17. The method of claim 16, further comprising:

inserting the tension member through a lumen of the tension device; and applying a tension force to a portion of the tension member extending proximally of the tension device.

18. A method for inhibiting migration of anchors of a heart implant device adjacent wall of a heart within a patient body, the method comprising:

positioning a first anchor in engagement with a first wall of the heart, the first anchor being coupled with a tension member;

positioning a second anchor in engagement with a second wall of the heart, the second anchor being slidably coupled with the tension member so that the second anchor may slide proximally and distally along length of the tension member;

engaging the second anchor with a tension device in a first mode of operation to urge the first wall toward the second wall;

normalizing a force indicator of the tension device;

applying an anchor force to the second anchor with the tension device in a second mode of operation so that the first anchor provides a force urging the firs wall toward the second wall and the second anchor provides a force urging the second wall toward the first wall, wherein the tension device in the second mode of operation indicates the anchor force that is applied to the second anchor; and securing the second anchor relative to the tension member while the anchor force is applied so as to restrict proximal movement of the second anchor along the tension member and maintain the anchor force.

19. The method of claim 18, wherein the second anchor comprises a variable force mode that allows the second anchor to slide axially along the tension member, and wherein the second anchor further comprises a set force mode that inhibits proximal movement of the second anchor along the tension member.

20. The method of claim 19, wherein the second anchor comprises a lumen though which the tension member is inserted and a lock, and wherein the method further comprises operating the lock to reconfigure the second anchor from the variable force mode to the set force mode, or vice versa.

21. The method of claim 19, wherein the second anchor is reconfigured from outside the patient body.

22. The method of claim 18, wherein the first anchor is inserted over a guidewire.

23. The method of claim 22, wherein the first anchor is inserted in a low profile configuration, and wherein the first anchor is deployable laterally relative to the tension member to a deployed configuration.

24. The method of claim 18, wherein the tension device comprises a shaft extending from a proximal end to a distal end and a lumen through which the tension member is inserted, and wherein the anchor force is applied by tensioning a portion of the tension member extending proximally of the tension device.

25. The method of claim 24, wherein the tension device further comprises a tube slidably disposed over the shaft, the tube including a compression spring and indicia that provide an indication of the anchor force applied.

26. The method of claim 18, wherein the anchor force is sufficient to bring the first wall into engagement with the second wall, and is insufficient to induce passage of the first anchor through the first wall.

27. The method of claim 18, wherein the anchor force comprises a force of between about 2N and about 6N.

28. The method of claim 18, wherein the anchor force comprises a force of between about 3N and about 4N.

29. The method of claim 28, wherein the tension device is configured such that the anchor force cannot exceed 4N.

30. The method of claim 18, further comprising advancing an intermediate body of an ingrowth material along the tension member so that the intermediate body of an ingrowth material is disposed between the first wall and the second wall, extending the intermediate body of an ingrowth material laterally from the tension member, and rotationally orientating the intermediate body of an ingrowth material by rotating the tension member.

* * * * *